(12) United States Patent
Toyooka et al.

(10) Patent No.: US 8,198,447 B2
(45) Date of Patent: Jun. 12, 2012

(54) FUSED TRICYCLIC COMPOUND HAVING ALDOSE REDUCTASE INHIBITORY ACTIVITY

(75) Inventors: Naoki Toyooka, Toyama (JP); Atsushi Kato, Toyama (JP); Isao Adachi, Toyama (JP)

(73) Assignee: National University Corporation University of Toyama (JP)

( * ) Notice: Subject to any disclaimer, the term of this patent is extended or adjusted under 35 U.S.C. 154(b) by 357 days.

(21) Appl. No.: 12/704,051

(22) Filed: Feb. 11, 2010

(65) Prior Publication Data

US 2010/0145052 A1    Jun. 10, 2010

Related U.S. Application Data

(63) Continuation of application No. PCT/JP2008/072942, filed on Dec. 17, 2008.

(30) Foreign Application Priority Data

Dec. 18, 2007  (JP) ................. 2007-325944
Oct. 24, 2008  (JP) ................. 2008-273685

(51) Int. Cl.
    C07D 471/04    (2006.01)
    C07D 491/052   (2006.01)
    C07D 495/04    (2006.01)
(52) U.S. Cl. ............. 546/86; 548/421; 548/432
(58) Field of Classification Search .......... None
    See application file for complete search history.

(56) References Cited

FOREIGN PATENT DOCUMENTS

| WO | WO2005/115470 | 12/2005 |
| WO | WO2006/011750 | 2/2006 |
| WO | WO2006/058088 | 6/2006 |

OTHER PUBLICATIONS

"The Polyol Pathway Renaissance—New Perspective of Polyol Pathway and Expanded Clinical Application of Aldose Reductase Inhibitor—" by S. Yagihashi Diabetes Complications, vol. 21 (1), pp. 25-32 (2007).
"Synthese von 4.9-Dihydropyrano[3.4-b]indol-1(3H)-onen aus α-Ethoxalyl-γ-lactonen" by Jochen Lehmann, Khadiga M. Ghoneim, Bothaina Abd El-Fattah and Adel A. El-Gendy, Arch. Pharm., 320, pp. 22-29 (1987).
"Autoxidation of Intermediary Mesoionic 1,3-Oxazolium-5-olates Generated from Cyclic N-Acryl α-Amino Acids" by M. Kawase, Chem. Pharm. Bull., 45(8), pp. 1248-1253 (1997).

Miyamoto, Shuichi, "Recent Advances in Aldose Reductase Inhibitors: Potential Agents for the Treatment of Diabetic Complications", Expert Opinion on Therapeutic Patents, Informa Healthcare, GB, vol. 12, No. 5, pp. 621-631 (Jan. 1, 2002).

Primary Examiner — Rebecca Anderson
Assistant Examiner — Alicia L Otton
(74) Attorney, Agent, or Firm — Harness, Dickey & Pierce, P.L.C.

(57) ABSTRACT

A fused tricyclic compound having aldose reductase inhibitory activity and shown by the following formula,

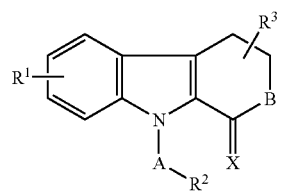

wherein $R^1$ represents 1 to 3 atoms or substituents selected from a hydrogen atom, a halogen atom, a substituted or unsubstituted alkyl, cycloalkyl, alkylene, or alkoxy group, and a protected or unprotected hydroxyl or carboxyl group, $R^2$ represents a protected or unprotected carboxyl group, $R^3$ represents 1 or 2 atoms or substituents selected from a hydrogen atom, a halogen atom, an oxo group, a substituted or unsubstituted alkyl or alkoxy group, and a protected or unprotected carboxyl group, A represents an alkylene group, and B represents an oxygen atom, a sulfur atom, or a group shown by the following formula,

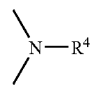

wherein $R^4$ represents an alkyl or aryl group substituted by an aryl, cycloalkyl, or heterocyclic group, and X represents an oxygen atom or a sulfur atom, provided that, when B represents a group shown by the following formula:

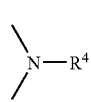

(III)

wherein $R^4$ represents an alkyl or aryl group substituted with an aryl, cycloalkyl, or heterocyclic group, X represents a sulfur atom.

9 Claims, No Drawings

FUSED TRICYCLIC COMPOUND HAVING ALDOSE REDUCTASE INHIBITORY ACTIVITY

CROSS REFERENCE TO RELATED APPLICATION

This application is a continuation of International Patent Application No. PCT/JP2008/72942, having an international filing date of Dec. 17, 2008, which designated the United States, the entirety of which is incorporated herein by reference. Japanese Patent Application Nos. 2007-325944 filed on Dec. 18, 2007 and 2008-273685 filed on Oct. 24, 2008 are also incorporated herein by reference in their entirety.

BACKGROUND

The present invention relates to a fused tricyclic compound having aldose reductase inhibitory activity. More particularly, the invention relates to a β-carboline derivatives and a 1,3,4,9-tetrahydropyrano[3,4-b]indole derivatives having aldose reductase inhibitory activity, an aldose reductase inhibitor comprising these compounds, and a therapeutic agent comprising these compounds as the main component.

The complications of diabetes include neurosis, retinopathy, nephropathy, and the like. 10% of diabetics are afflicted by various types of complication in about ten years. 30 to 50% of diabetic patients are said to have these types of complication in 30 years.

There is a polyol pathway metabolic increase as a factor of promoting the complications of diabetes.

The polyol pathway is catalyzed by an aldose reductase and a sorbitol dehydrogenase.

The amount converted from glucose into sorbitol is very small at a normal blood glucose concentration. However, aldose reductase is activated in hyperglycemia and increases the amount of glucose flowing into the polyol pathway, resulting in an increase in the amount of production of sorbitol and fructose.

Inflow of glucose into cells easily takes place in insulin-independent organizations. Sorbitol and fructose produced in the cells are excreted only with difficulty and accumulated in the cells due to their low permeability through cell membranes.

Although nerve tissue cells, capillary wall cells, and mesangial cells are mainly involved in neurosis, retinopathy, and nephropathy, respectively, these diseases are thought to be induced by accumulation of sorbitol and a metabolic disorder of myoinositol.

Myoinositol is a component of phosphoinositide and presents in these cells at a high concentration.

Myoinositol and glucose compete each other when incorporated into cells. As a result, hyperglycemia is believed to be a cause of myoinositol reduction.

Myoinositol reduction reduces Na/K ATPase activity and causes the complications of diabetes.

Moreover, progress of research is proving that polyol metabolism is activated not only by a hyperglycemia state but also by an ischemia-reperfusion state and increased oxidative stress. Thus, the applicability of an aldose reductase inhibitor to various diseases such as arteriosclerosis, ischemia-reperfusion hindrance of the heart and brain, inflammation, sepsis, and cancer is now increasing as a main focus of attention (*Diabetes Complications*, Vol. 21 (1), 25-32 (2007)).

As a therapeutic agent having an aldose reductase inhibitory effect, therapeutic agents containing a compound having a carboxymethyl group structure in the molecule such as epalrestat, zenarestat, and alrestatin, therapeutic agents containing a hydantoin derivative such as sorbinil, idarestat, and ranirestat, and the like have been known.

On the other hand, a compound having a tetrahydro β-carboline derivative, particularly 2,3,4,9-tetrahydro-β-carbolin-1-one, as a mother nucleus, has been known as an antagonist of cyclin dependent kinases (WO2006/011750).

SUMMARY

Aldose reductase inhibitors such as epalrestat and ranirestat have been developed for the purpose of treating diabetic neuropathy. However, as the progress of aldose reductase activity was reported to have an influence on the growth of various cancer cells including colorectal cancer in recent years, development of an aldose reductase inhibitor having a different molecular structure has been desired.

The inventors of the invention studied fused tricyclic compounds such as rhetsinine and the like which are a component of mandarin orange medicinal herb and a component of Evodia.

The inventors synthesized various compounds having a carboxyalkyl group such as carboxymethyl in the molecular structure and found that these compounds have aldose reductase inhibitory activity. As a result, the inventors completed the invention.

DESCRIPTION OF EXEMPLARY EMBODIMENTS

The invention will be described in detail below.

The following terms as used in the invention have the following meanings unless otherwise indicated.

A halogen atom refers to a fluorine atom, a chlorine atom, a bromine atom, or an iodine atom. An alkyl group refers to a linear or branched alkyl group having 1 to 12 carbon atoms such as a methyl, ethyl, propyl, iso-propyl, butyl, iso-butyl, tert-butyl, pentyl, or hexyl group. A lower alkyl group refers to a linear or branched alkyl group having 1 to 6 carbon atoms such as a methyl, ethyl, propyl, iso-propyl, butyl, iso-butyl, tert-butyl, pentyl, or hexyl group. An alkylene group refers to a linear or branched alkylene group having 1 to 6 carbon atoms such as a methylene, ethylene, propylene, or iso-propylene group. A cycloalkyl group refers to a cyclopropyl, cyclobutyl, cyclopentyl, or cyclohexyl group. An alkoxy group refers to a linear or branched alkoxy group having 1 to 12 carbon atoms such as a methoxy, ethoxy, propoxy, iso-propoxy, butoxy, iso-butoxy, tert-butoxy, pentyloxy, hexyloxy, heptyloxy, or octyloxy group. A lower alkyloxy group refers to a linear or branched alkyloxy group having 1 to 6 carbon atoms such as a methoxy, ethoxy, propoxy, iso-propoxy, butoxy, iso-butoxy, tert-butoxy, pentyloxy, or hexyloxy group. An aryl group refers to a phenyl, naphthyl, indanyl, indenyl, or the like group. An acyl group refers to a formyl, alkylcarbonyl, or aroyl group. An alkylcarbonyl group refers to an alkylcarbonyl group having 2 to 6 carbon atoms such as an acetyl group or a propionyl group. An aroyl group refers to an arylcarbonyl group such as a benzoyl group or a naphthylcarbonyl group.

A heterocyclic group refers to a six membered or five membered ring, fused ring, or crosslinked ring containing at least one hetero atom selected from the group consisting of a nitrogen atom, an oxygen atom, and a sulfur atom such as a pyrrolidinyl, piperidinyl, piperazinyl, homopiperazinyl, homopiperidinyl, morpholyl, thiomorpholyl, tetrahydroquinolinyl, tetrahydro isoquinolyl, quinuclidinyl, imidazolinyl, pyrrolyl, imidazolyl, pyrazolyl, pyridyl, pyrimidyl, quinolyl, quinolidinyl, thiazolyl, tetrazolyl, thiadiazolyl, pyrrolinyl, pyrrazolinyl, pyrazolidinyl, purynyl, furyl, thienyl, benzothienyl, pyranyl, isobenzofuranyl, oxazolyl, isooxazolyl, benzofuranyl, indolyl, benzimidazolyl, benzoxazolyl, benzoisooxazolyl, benzothiazolyl, quinoxalyl, dihydroquinoxalyl, 2,3-dihydrobenzothienyl, 2,3-dihydrobenzopyrrolyl, 2, 3-4H-1-thianaphthyl, 2,3-dihydrobenzofuranyl, benzo[b]dioxanyl, imidazo[2,3-a]pyridyl, benzo[b]piperazinyl, chromenyl, isothiazolyl, isooxazolyl, oxadiazolyl, pyridazinyl, isoindolyl, or isoquinolyl group.

A carboxyl protecting group refers to all groups usable as a protective group of a general carboxyl group and includes, for example, a lower alkyl group such as a methyl, ethyl, propyl, iso-propyl, 1,1-dimethylpropyl, butyl, or tert-butyl group, an aryl group such as a phenyl group or a naphthyl group, an aryl lower alkyl group such as a benzyl, diphenylmethyl, trityl, p-nitrobenzyl, p-methoxybenzyl, or bis(p-methoxyphenyl)methyl group, an acyl lower alkyl group such as an acetylmethyl, benzoylmethyl, p-nitrobenzoylmethyl, p-bromobenzoylmethyl, or p-methanesulfonylbenzoylmethyl group, an oxygen-containing heterocyclic group such as a 2-tetrahydropyranyl group or a 2-tetrahydrofuranyl group, a halogeno lower alkyl group such as a 2,2,2-trichloroethyl group, a lower alkylsilyl-lower alkyl group such as a 2-(trimethylsilyl)ethyl group, a lower alkylsilyl-lower alkyl group such as a 2-(trimethylsilyl)ethyl group, a nitrogen-containing heterocyclic lower alkyl group such as a phthalimidemethyl group or a succinimidemethyl group, a cycloalkyl group such as a cyclohexyl group, a lower alkoxy-lower alkyl group such as a methoxymethyl, methoxyethoxymethyl, or 2-(trimethylsilyl)ethoxymethyl group, an aryl lower alkoxy-lower alkyl group such as a benzyloxymethyl group, a lower alkylthio-lower alkyl group such as a methylthiomethyl group or a 2-methylthioethyl group, an arylthio-lower alkyl group such as a phenylthiomethyl group, a lower alkenyl group such as a 1,1-dimethyl-2-propenyl, 3-methyl-3-butenyl, or allyl group, and a substituted silyl group such as a trimethylsilyl, triethylsilyl, tri-isopropylsilyl, diethylisopropylsilyl, tert-butyldimethylsilyl, tert-butyldiphenylsilyl, diphenylmethylsilyl, or tert-butylmethoxyphenylsilyl group.

A hydroxyl protecting group refers to all groups usable as a protective group of a general hydroxyl group and include, for example, an acyl group such as a benzyloxycarbonyl, 4-nitrobenzyloxycarbonyl, 4-bromobenzyloxycarbonyl, 4-methoxybenzyloxycarbonyl, 3,4-dimethoxybenzyloxycarbonyl, methoxycarbonyl, ethoxycarbonyl, tert-butoxycarbonyl, 1,1-dimethylpropoxycarbonyl, isopropoxycarbonyl, isobutyloxycarbonyl, diphenylmethoxycarbonyl, 2,2,2-trichloroethoxycarbonyl, 2,2,2-tribromoethoxycarbonyl, 2-(trimethylsilyl)ethoxycarbonyl, 2-(phenylsulfonyl)ethoxycarbonyl, 2-(triphenylphosphonio)ethoxycarbonyl, 2-furfuryloxycarbonyl, 1-adamantyloxycarbonyl, vinyloxycarbonyl, allyloxycarbonyl, S-benzylthiocarbonyl, 4-ethoxy-1-naphthyloxycarbonyl, 8-quinolyloxycarbonyl, acetyl, formyl, chloroacetyl, dichloroacetyl, trichloroacetyl, trifluoroacetyl, methoxyacetyl, phenoxyacetyl, pivaloyl, or benzoyl group, a lower alkyl group such as a methyl, tert-butyl, 2,2,2-trichloroethyl, or 2-trimethylsilylethyl group, a lower alkenyl group such as an allyl group, an aryl lower alkyl group such as a benzyl, p-methoxybenzyl, 3,4-dimethoxybenzyl, diphenylmethyl, or trityl group, an oxygen- or sulfur-containing heterocyclic group such as a tetrahydrofuryl, tetrahydropyranyl, or tetrahydrothiopyranyl group, a lower alkoxy- or lower alkylthio-lower alkyl group such as a methoxymethyl, methylthiomethyl, benzyloxymethyl, 2-methoxyethoxymethyl, 2,2,2-trichloroethoxymethyl, 2-(trimethylsilyl)ethoxymethyl, 1-ethoxyethyl, or 1-methyl-1-methoxyethyl group, a lower alkyl- or aryl-sulfonyl group such as a methanesulfonyl group or a p-toluenesulfonyl group, and a substituted silyl group such as a trimethylsilyl, triethylsilyl, triisopropylsilyl, diethyliso-propylsilyl, tert-butyldimethylsilyl, tert-butyldiphenylsilyl, diphenylmethylsilyl, or tert-butylmethoxyphenylsilyl group.

The invention provides a fused tricyclic compound shown by the following formula [1] or a salt thereof, and an aldose reductase inhibitor comprising the fused tricyclic compound shown by the following formula [1] or a salt thereof,

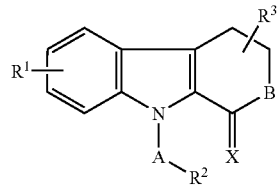

[1]

wherein $R^1$ independently represents 1 to 3 atoms or substituents selected from a hydrogen atom, a halogen atom, a substituted or unsubstituted alkyl, cycloalkyl, alkylene, or alkoxy group, and a protected or unprotected hydroxyl or carboxyl group, two or three atoms or groups, if present, being either the same or different, $R^2$ represents a protected or unprotected carboxyl group, $R^3$ independently represents 1 or 2 atoms or substituents selected from a hydrogen atom, a halogen atom, an oxo group, a substituted or unsubstituted alkyl or alkoxy group, and a protected or unprotected carboxyl group, A represents an alkylene group, B represents an oxygen atom, a sulfur atom, or a group shown by the following formula,

wherein $R^4$ represents an alkyl or aryl group substituted with an aryl, cycloalkyl, or heterocyclic group, and X represents an oxygen atom or a sulfur atom, provided that, when B represents a group shown by the following formula:

(III)

wherein $R^4$ represents an alkyl or aryl group substituted with an aryl, cycloalkyl, or heterocyclic group, X represents a sulfur atom.

The fused tricyclic compound shown by the formula [1] may be used in the form of a salt.

As a salt of the compound shown by the formula [1], a salt of a commonly known basic group such as an amino group or a salt of a commonly known acidic group such as a hydroxyl group or a carboxyl group can be given.

As examples of a salt of a basic group, a salt with a mineral acid such as hydrochloric acid, hydrobromic acid, or sulfuric acid, a salt with an organic carboxylic acid such as formic acid, acetic acid, citric acid, oxalic acid, fumaric acid, maleic acid, malic acid, tartaric acid, aspartic acid, trichloroacetic acid, or trifluoroacetic acid, and a salt with a sulfonic acid such as methanesulfonic acid, benzenesulfonic acid, p-toluenesulfonic acid, mesitylenesulfonic acid, or naphthalenesulfonic acid can be given. As examples of a salt of an acidic group, a salt with an alkali metal such as sodium or potassium, a salt with an alkaline earth metal such as calcium or magnesium, an ammonium salt, and a salt with a nitrogen-containing organic base such as trimethylamine, triethylamine, tributylamine, pyridine, N,N-dimethylaniline, N-methylpiperidine, N-methylmorpholine, diethylamine, dicyclohexylamine, procaine, dibenzylamine, N-benzyl-β-phenethylamine, 1-ephenamine, or N,N-dibenzylethylenediamine can be given.

A pharmacologically acceptable salt is preferable among the salts mentioned above.

The fused tricyclic compound of the invention includes all isomers, such as an optical isomer, a geometrical isomer, or a tautomer, of the fused tricyclic compound shown by the formula [1] or a salt thereof, as well as hydrates, solvates, and all crystal forms.

The fused tricyclic compound of the invention includes a 1,3,4,9-tetrahydropyrano[3,4-b]indole derivative shown by the following formula [1a] or a salt thereof,

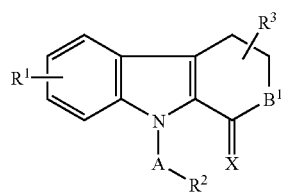

[1a]

wherein $B^1$ represents O or S, and $R^1$, $R^2$, $R^3$, A, and X are the same as defined above, and a tetrahydro-β-carboline derivative shown by the following formula [1b] or a salt thereof,

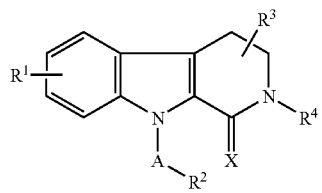

[1b]

wherein $R^4$ represents an alkyl or aryl group substituted by an aryl, cycloalkyl, or heterocyclic group, and $R^1$, $R^2$, $R^3$, A, and X are the same as defined above.

The following compounds or salts thereof can be given as preferable examples of compounds of the invention.

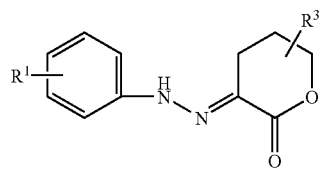

[2]

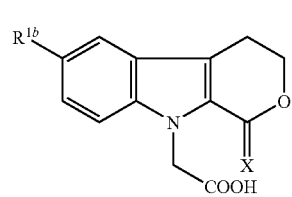

[1aa]

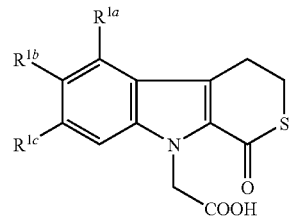

[1ab]

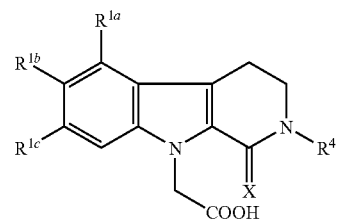

[1ba]

$R^{1b}$ in the formulas [1aa], [1ab], and [1ba] represents a hydrogen atom, a halogen atom, a substituted or unsubstituted alkyl, cycloalkyl, or alkoxy group, or a protected or unprotected hydroxyl group, $R^4$ represents an alkyl or aryl group substituted by an aryl, cycloalkyl, or heterocyclic group, and X represents an oxygen atom or a sulfur atom.

$R^{1a}$, $R^{1b}$, and $R^{1c}$ in the formula [1ab] individually represent a hydrogen atom, a halogen atom, a substituted or unsubstituted alkyl group, a cycloalkyl group, or a substituted or unsubstituted alkoxy group, or $R^{1a}$ and $R^{1b}$ or $R^{1b}$ and $R^{1c}$ in combination form an alkylene group.

$R^{1a}$ and $R^{1c}$ in the formula [1ab] individually represent a hydrogen atom or a halogen atom, and $R^{1b}$ represents a hydrogen atom, a halogen atom, a substituted or unsubstituted alkyl group, a cycloalkyl group, a substituted or unsubstituted alkoxy group, or a hydroxyl group.

The fused tricyclic compound shown by the formula [1] can be prepared by the following method.

Preparation of 1,3,4,9-tetrahydropyrano[3,4-b]indole derivative

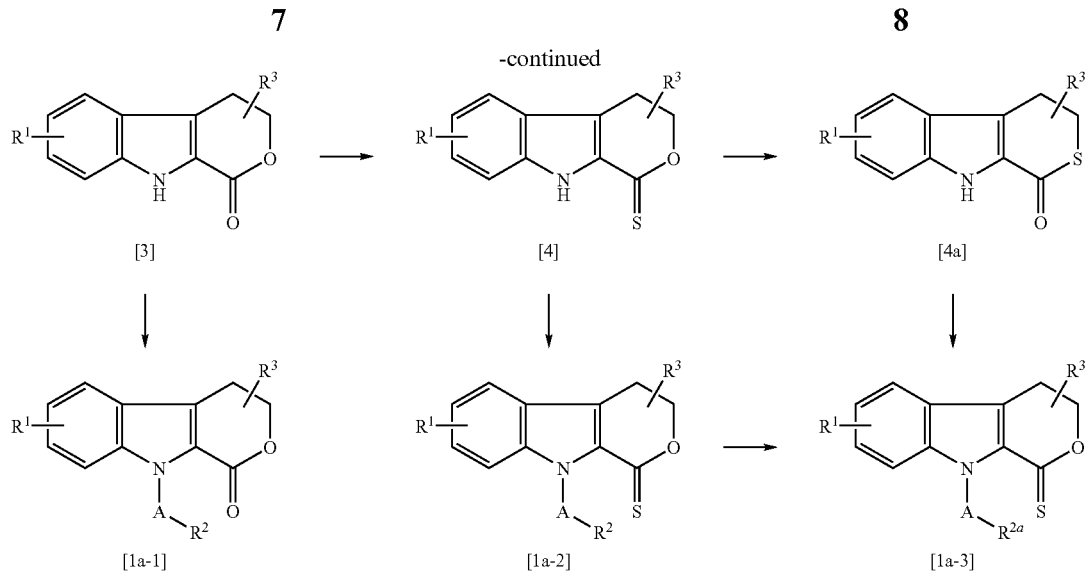

In the above Scheme, $R^{2a}$ represents a hydrogen atom and $R^1$, $R^2$, $R^3$, A, and X are the same as defined above.

A compound shown by the formula [3] can be prepared from a compound shown by the formula [2] according to the method described in *Arch. Pharm.*, 320, 22-29 (1987), for example.

A compound shown by the formula [4] can be prepared by thiolactamization of the compound shown by the formula [3] using Lawesson's reagent.

A compound shown by the formula [1a-1], a compound shown by the formula [1a-2], and a compound shown by the formula [1a-3] whose $R^2$ is protected carboxylic acid can be prepared by reacting the compound shown by the formula [3], the compound shown by the formula [4], or the compound shown by the formula [4a] with a halogeno lower fatty acid ester such as t-butyl bromoacetate, ethyl bromoacetate, or methyl bromoacetate.

Further, the compound of the formula [1a-1] or the compound of the formula [1a-2] in which $R^2$ is a carboxylic acid can be prepared by removing the carboxylic acid protective group by dealkylation using trimethylsilyl iodide, or hydrolysis.

A compound shown by the formula [4a] or a compound shown by the formula [1a-3] can be prepared by treating the compound shown by the formula [4] or the compound shown by the formula [1a-2] with trimethylsilyl iodide under reflux with heating of a dichloroethane solution, for example.

Preparation of tetrahydro-β-carboline Derivative

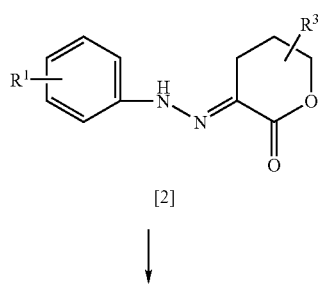

In the above Scheme, $R^1$, $R^2$, $R^3$, $R^4$, A, and X are the same as defined above.

A compound shown by the formula [3] can be prepared from a compound shown by the formula [2] according to the method described in *Arch. Pharm.*, 320, 22-29 (1987), for example.

A compound shown by the formula [5] can be prepared by reacting various amines with a compound shown by the formula [3].

A compound shown by the formula [6] can be prepared by thiolactamization of a compound shown by the formula [5] using Lawesson's reagent.

A compound shown by the formula [1b-1] or a compound shown by the formula [1b-2] which are carboxylic acids in which $R^2$ is protected can be prepared by reacting the compound shown by the formula [5] or the compound shown by the formula [6] with a halogeno lower fatty acid ester such as t-butyl bromoacetate or methyl bromoacetate.

Further, the compound of the formula [1b-1] or the compound of the formula [1b-2] in which $R^2$ is a carboxylic acid can be prepared by removing the carboxylic acid protective group by dealkylation using trimethylsilyl iodide, or hydrolysis.

Preparation of tetrahydro-β-carboline derivative (2)

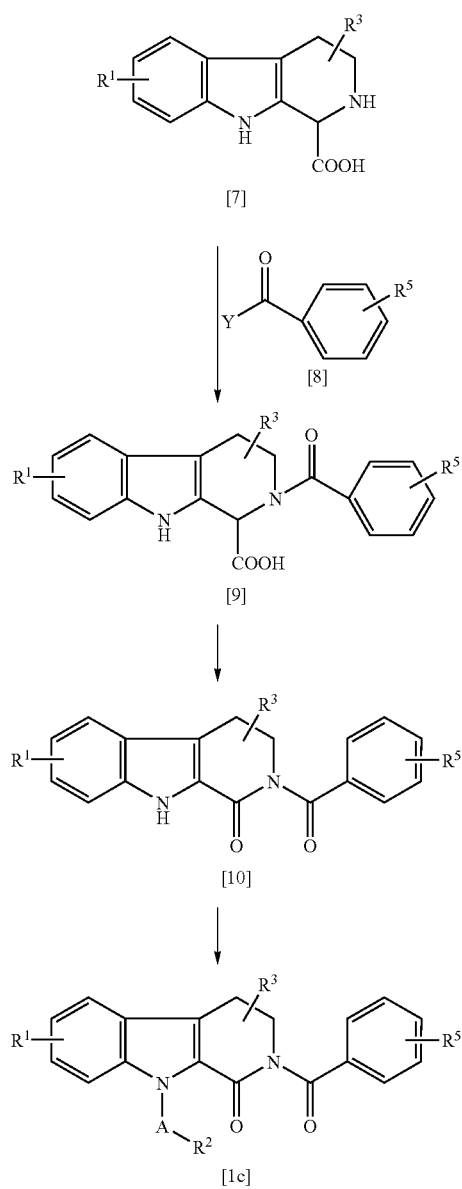

In the above Scheme, $R^5$ individually represents a hydrogen atom, a halogen atom, an alkyl group, an alkoxy group, or a hydroxyl group, Y represents a halogen atom, and $R^1$, $R^2$, $R^3$, $R^4$, and A are the same as defined above.

A compound shown by the formula [9] can be prepared by reacting a compound shown by the formula [7] with a compound shown by the formula [8] in the presence of a base such as sodium hydroxide.

A compound shown by the formula [10] can be prepared from a compound shown by the formula [9] according to the method described in *Chem. Pharm. Bull.*, 45, 1248-1253 (1997), for example.

A compound shown by the formula [1c] which is a carboxylic acid in which $R^2$ is a protected carboxylic group can be prepared by reacting the compound shown by the formula [10] with a halogeno lower fatty acid ester such as t-butyl bromoacetate, ethyl bromoacetate, or methyl bromoacetate.

Further, a compound shown by the formula [1c] in which $R^2$ is a carboxylic acid can be prepared by removing the carboxylic acid protective group by dealkylation using trimethylsilyl iodide, or hydrolysis.

In the compounds shown by the formulas [2] to [10], those having a hydroxyl group, an amino group, or a carboxyl group can be reacted by previously protecting the hydroxyl group, amino group, or carboxyl group with a general protecting group. After the reaction, these protective groups may be removed by a general method.

When the compounds shown by the formulas [2] to [6] have isomers (such as an optical isomer, a geometrical isomer, a tautomer, and the like), all these isomers may be used. In addition, hydrates, solvates, and crystal forms of these compounds may also be used.

The compounds shown by the formulas [2] to [6] may be used as is without isolation.

The compounds shown by the formulas [1a-1], [1a-2], [1a-3], [1b-1], [1b-2], and [1c] can be isolated and purified by a general method such as extraction, crystallization, distillation, and column chromatography.

The compound of the invention can be made into therapeutic agent preparations such as an oral preparation (tablet, capsule, powder, granule, subtle granules, pill, suspension, emulsion, liquid preparation, syrup, etc.), injection, suppository, a preparation for external application (ointment, pasting agent, etc.), an aerosol agent, and the like by mixing with various therapeutic agent additives such as an excipient, a binder, a disintegrator, a decay inhibitor, a binder and anti-sticking agent, a lubricant, an absorption/adsorption carrier, a solvent, an extender, an isotonizing agent, a solubilizer, an emulsifier, a suspending agent, a thickener, a coating agent, an absorption promoter, a gelling agent/coagulation promoter, an optical stabilizer, a preservative, a desiccant, an emulsification/suspension/dispersion stabilizer, a color protection agent, a deoxidizer/antioxidant, a flavor agent, a forming agent, a deodorant, a coloring agent, a defoamer, a soothing agent, an antistatic agent, a buffering agent, a pH regulator, and the like.

The method of administration of the above preparations is not particularly limited and may be appropriately determined according to the type of preparation, the age, sex, and other conditions of the patient, and symptoms of the patient.

Although a dose of the effective component of the preparation of the invention is appropriately selected according to the application, the age, sex, disease of the patient, and other conditions, usually an amount of 0.1 to 500 mg per day per adult is administered at one time or several times a day.

Next, pharmacological effects of typical compounds of the invention will be described.

Test Example 1

Aldose Reductase Inhibitory Activity

A reaction solution containing a 200 mM of a phosphate buffer solution (pH 6.2), 1.5 mM of reduced nicotinamide adenine dinucleotide phosphate (NADPH), 1 mg/ml of bovine serum albumin, a test compound, and 100 mM of DL-glyceraldehyde as a substrate was prepared. Aldose reductase II ($5.1 \times 10^{-1}$ unit/ml) was added to the solution to initiate the reaction, and the amount of NADPH reduced by the reaction was measured at an absorption wavelength of 340 nm using a spectrophotometer.

The results are shown in Tables 1 to 5.

The epalrestat IC$_{50}$ value in the above assay system was 0.7 μM.

TABLE 1

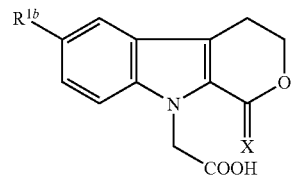

| COMPOUND | R$^{1b}$ | X | IC$_{50}$ (μM) |
|---|---|---|---|
| 30 | Cl | O | 12.4 |
| 31 | Cl | S | 11.1 |

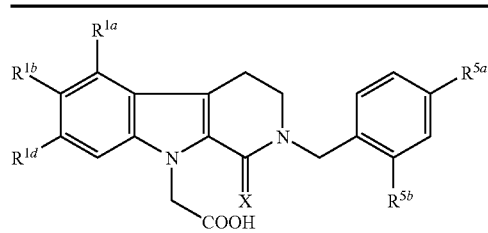

TABLE 2

| COMPOUND | R$^{1a}$ | R$^{1b}$ | R$^{1c}$ | X | R$^{5a}$ | R$^{5b}$ | IC$_{50}$ (μM) |
|---|---|---|---|---|---|---|---|
| 22 | H | F | H | O | H | H | 51.5 |
| 23 | H | F | H | S | H | H | 5.6 |
| 24 | H | F | H | S | F | H | 13.6 |
| 25 | H | F | H | O | F | H | 48.6 |
| 26 | H | H | H | S | H | H | 4.2 |
| 27 | H | Cl | H | S | H | H | 5.0 |
| 28 | F | H | F | S | H | H | 2.5 |
| 29 | H | OCH$_3$ | H | S | H | H | 5.7 |
| 32 | H | Br | H | S | H | H | 6.2 |
| 37 | H | H | Cl | S | Br | F | 27.4 |
| 38 | H | H | Cl | S | H | H | 3.7 |
| 39 | F | H | F | S | Br | F | 21.1 |
| 40 | H | OH | H | S | H | H | 4.8 |
| 42 | H | OCH$_2$CO$_2$H | H | S | H | H | 2.6 |

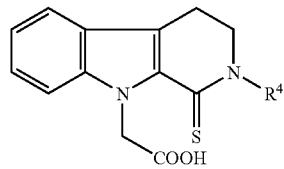

TABLE 3

| COMPOUND | R$^4$ | IC$_{50}$ (μM) |
|---|---|---|
| 33 | (phenyl) | 36.3 |
| 34 | (ethylcyclohexyl) | 7.2 |
| 35 | (ethylfuryl) | 16.3 |

TABLE 3-continued

| COMPOUND | R$^4$ | IC$_{50}$ (μM) |
|---|---|---|
| 36 | (ethylthienyl) | 7.6 |

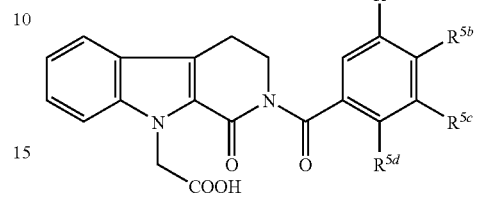

TABLE 4

| COMPOUND | R$^{5a}$ | R$^{5b}$ | R$^{5c}$ | R$^{5d}$ | IC$_{50}$ (μM) |
|---|---|---|---|---|---|
| 46 | H | F | H | H | 21.7 |
| 47 | H | Br | H | H | 34.6 |
| 48 | H | OCH$_3$ | H | H | 35.8 |
| 49 | H | F | H | F | 45.3 |
| 50 | F | H | F | H | 34.5 |
| 51 | H | Br | H | F | 68.3 |
| 52 | F | F | F | H | 55.3 |
| 53 | OCH$_3$ | OCH$_3$ | OCH$_3$ | H | 46.8 |
| 54 | OH | OH | OH | H | 48.0 |
| 55 | H | H | H | H | 53.1 |

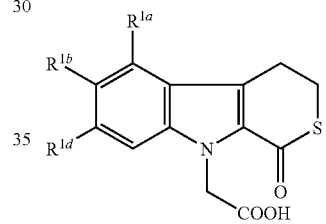

TABLE 5

| COMPOUND | R$^{1a}$ | R$^{1b}$ | R$^{1c}$ | IC$_{50}$ (μM) |
|---|---|---|---|---|
| 56 | H | Cl | H | 1.1 |
| 57 | H | H | H | 2.8 |
| 58 | H | CH$_3$ | H | 1.6 |
| 59 | H | CH(CH$_3$)$_3$ | H | 1.4 |
| 60 | H | CH$_2$(phenyl) | H | 3.6 |
| 61 | H | OCH$_3$ | H | 2.6 |
| 62 | H | (cyclohexyl) | H | 5.6 |
| 63 | CH$_3$ | H | CH$_3$ | 5.9 |
| 64 | Cl | H | H | 3.6 |
| 65 | H | —(CH$_2$)$_4$— | | 3.4 |
| 66 | —(CH$_2$)$_4$— | | H | 1.0 |

Test Example 2

Measurement of Sorbitol Dehydrogenase

A reaction solution containing a 100 mM of a Tris-HCl buffer solution (pH 9.0), 0.2 mM of oxidized nicotinamide adenine dinucleotide phosphate (NAD+), 1 mg/ml of bovine serum albumin, 100 μM of a test compound, and 500 mM of sorbitol as a substrate was prepared. Sorbitol dehydrogenase (1.28 unit/ml) was added to the solution to initiate the reaction, and the amount of NAD reduced to NADH by the reaction was measured at an absorption wavelength of 340 nm using a spectrophotometer.

The results are shown in Table 6.

The cell suspension ($1.35 \times 10^4$ cells/ml) was added to a 96 well plate, 100 μl per well.

After culturing under the conditions of 37° C. and 5% $CO_2$ for 16 hours, a solution of the test compound dissolved in DMSO to a concentration of 25 μM was added, followed by continuation of culture for a further 44 hours, while only DMSO was added to a control to continue the culture.

TABLE 6

| COMPOUND | $R^{1b}$ | $R^{1b}$ | $R^{1b}$ | X | B | $IC_{50}$ (μM) |
|---|---|---|---|---|---|---|
| 26 | H | H | H | S | —N(—)—CH$_2$—Ph | 33.0 |
| 28 | F | H | F | S | —N(—)—CH$_2$—Ph | 37.1 |
| 56 | H | Cl | H | O | S | 29.7 |
| 59 | H | C(CH$_3$)$_3$ | H | O | S | 33.8 |
| 62 | H | cyclohexyl | H | O | S | 34.6 |
| 66 | —(CH$_2$)$_4$— | | H | O | S | 20.6 |

Test Example 3

Cancer Cell Sensitivity Test

Cells of mouse leukemia adriamycin sensitive strain P388/S were cultured in an RPMI1640 culture medium (5% fetal bovine serum, 20 mM 2-mercaptoethanol, 30 μM kanamycin) under conditions of 37° C. and 5% $CO_2$, and used for a compound sensitivity test.

After culturing, a phosphate buffered saline, adjusted to 2 mg/ml (PBS, pH 7.4), was added in an amount of 25 μl/well, followed by incubation for four hours to produce MTT-formazan.

After removing supernatant by aspiration, 200 μl of DMSO was added and the absorbance of MTT-formazan at 540 nm was measured. The results are shown in Table 7.

TABLE 7

| COMPOUND | $R^{1b}$ | $R^2$ | X | B | INHIBITORY RATE (%) |
|---|---|---|---|---|---|
| 22a | F | Et | O | —N(—)—CH$_2$—Ph | 34.5 |

TABLE 7-continued

| COMPOUND | $R^{1b}$ | $R^2$ | X | B | INHIBITORY RATE (%) |
|---|---|---|---|---|---|
| 23 | F | H | S | —N(—)—CH₂—Ph | 92.9 |
| 26 | H | H | S | —N(—)—CH₂—Ph | 88.1 |
| 30 | Cl | H | S | O | 31.1 |
| 52 | H | H | O | —N(—)—C(=O)—C₆H₂F₃ | 34.7 |

Test Example 4

Acute Toxicity Test

Compound 28 was orally administered to three mice at a dose of 500 mg/kg body weight, the maximum amount considered to be prescribed for the mouse in one dose.

As a result, all of the three mice survived with no abnormalities being observed in internal organs, action, etc.

Effects of the Invention

The β-carboline derivative and the 1,3,4,9-tetrahydropyrano[3,4-b]indole derivative which are the fused tricyclic compound of the invention exhibited aldose reductase inhibitory activity, while showing low sorbitol dehydrogenase inhibitory activity, demonstrating high enzyme selectivity. The compounds also exhibited high carcinoma inhibitory activity and low toxicity.

The invention will be described by way of examples, which should not be construed as limiting the invention.

EXAMPLES

Example 1

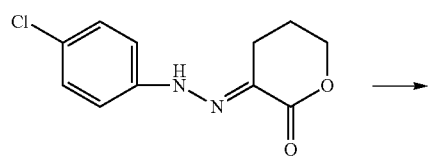

Ex.1 (A)

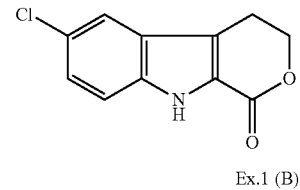

Ex.1 (B)

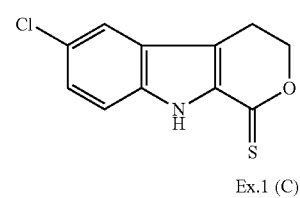

Ex.1 (C)

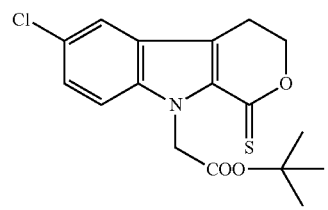

-continued

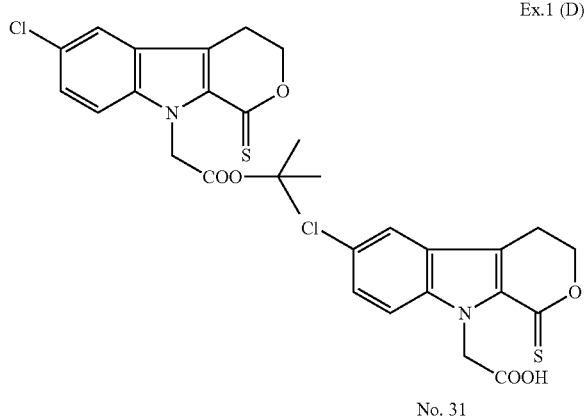

No. 31

(A) A 1 M hydrogen chloride acetic acid solution (40 ml) was added to an acetic acid (40 ml) solution of 3-[(4-chlorophenyl)hydrazono]tetrahydropyran-2-one (8.3 g, 34.8 mmol), followed by heating under reflux for 30 minutes.

After the addition of water (300 ml) to the reaction mixture while cooling with ice, the solid precipitated was collected by filtration, washed with water and hexane, and dried under reduced pressure to obtain 6-chloro-4,9-dihydro-3H-pyrano[3,4-b]indol-1-one (5.57 g, 72%) as an orange solid.

$^1$H NMR (500 MHz, DMSO-$d_6$) δ 3.08 (2H, t, J=7.2 Hz), 4.62 (2H, t, J=7.2 Hz), 7.33 (1H, d, J=7.8 Hz), 7.43 (1H, d, J=7.8 Hz), 7.80 (1H, s), 12.17 (1H, br)

(B) A Lawesson's reagent (164 mg, 0.41 mmol) was added to a toluene (7 ml) solution of 6-chloro-4,9-dihydro-3H-pyrano[3,4-b]indol-1-one (150 mg, 0.68 mmol), followed by heating under reflux for 15 hours. Then, toluene was evaporated off.

The residue was purified by silica gel column chromatography (silica gel: 15 g, eluate: methylene chloride) to obtain 6-chloro-4,9-dihydro-3H-pyrano[3,4-b]indole-1-thione (160 mg, 99%) as a light yellow solid.

mp: 172-175° C.

IR (KBr) 3220, 2986, 1597, 1537, 1472, 1260, 1216, 1074, 803 cm$^{-1}$ $^1$H NMR (500 MHz, CDCl$_3$) δ 3.15 (2H, t, J=6.4 Hz), 4.76 (2H, t, J=6.4 Hz), 7.35 (2H, m), 7.61 (1H, s), 8.88 (1H, br)

$^{13}$C NMR (75 MHz, CDCl$_3$) δ 20.98 (t), 71.17 (t), 113.51 (d), 114.86 (s), 120.99 (d), 125.67 (s), 126.91 (s), 127.94 (d), 132.90 (s), 137.04 (s), 198.10 (s)

(C) Sodium hydride (60%, 51.6 mg, 1.29 mmol) was added to a dimethyl formamide (5 ml) solution of 6-chloro-4,9-dihydro-3H-pyrano[3,4-b]indole-1-thione (279 mg, 1.17 mmol) wile cooling with ice, followed by stirring at room temperature for 30 minutes.

The reaction solution was cooled again to 0° C., and tert-butyl bromoacetate (0.21 ml, 1.40 mmol) was added. After stirring the mixture at room temperature for 17 hours, water (10 ml) was added to terminate the reaction.

The aqueous layer was extracted three times with ether (10 ml). The ether layers were combined. After drying with magnesium sulfate, the ether was evaporated off.

The residue was purified by silica gel column chromatography (silica gel 20 g, eluate: hexane:acetone=20:1) to obtain (6-chloro-1-thioxo-3,4-dihydro-1H-pyrano[3,4-b]indol-9-yl) acetic acid tert-butyl ester (267 mg, 65%) as a colorless solid.

IR (KBr) 2977, 1737, 1525, 1276, 1231, 1173, 1090 cm$^{-1}$ $^1$H NMR (500 MHz, CDCl$_3$) δ 1.45 (9H, s), 3.14 (2H, t, J=6.4 Hz), 4.68 (2H, t, J=6.4 Hz), 5.49 (2H, br), 7.21 (1H, d, J=9.0 Hz), 7.38 (1H, d, J=9.0 Hz), 7.63 (1H, s)

$^{13}$C NMR (75 MHz, CDCl$_3$) δ 21.41 (t), 28.17 (q), 47.08 (t), 70.21 (t), 82.66 (s), 111.56 (d), 115.03 (s), 117.66 (s), 120.83 (d), 123.60 (s), 127.21 (s), 128.06 (d), 139.29 (s), 167.19 (s), 196.52 (s)

(D) A chloroform (2 ml) solution of (6-chloro-1-thioxo-3,4-dihydro-1H-pyrano[3,4-b]indol-9-yl) (63 mg, 0.18 mmol) was added to a suspension obtained by adding trimethylsilyl iodide (0.1 ml, 0.72 mmol) to a chloroform (2 ml) suspension of sodium iodide (108 mg, 0.72 mmol) and stirring the mixture for 30 minutes. The resulting mixture was heated under reflux for three hours.

The aqueous layer was made acidic with 10% hydrochloric acid under cooling with ice and extracted with chloroform (10 ml×6). The chloroform layers were combined. After drying with magnesium sulfate, the chloroform was evaporated off.

The residue was purified by silica gel column chromatography (silica gel: 10 g, eluate: hexane:acetone=20:1 to 3:1) to obtain (6-chloro-1-thioxo-3,4-dihydro-1H-pyrano[3,4-b]indol-9-yl) acetic acid as a colorless solid (Compound 31, 37 mg, 70%).

IR (KBr) 3062, 2943, 1712, 1527, 1440, 1279, 1254, 1204, 1173, 1092 cm$^{-1}$ $^1$H NMR (500 MHz, DMSO-$d_6$) δ 3.21 (2H, t, J=6.3 Hz), 4.65 (2H, t, J=6.3 Hz), 5.58 (2H, br), 7.45 (1H, d, J=7.1 Hz), 7.67 (1H, d, J=7.1 Hz), 7.92 (1H, s)

Example 2

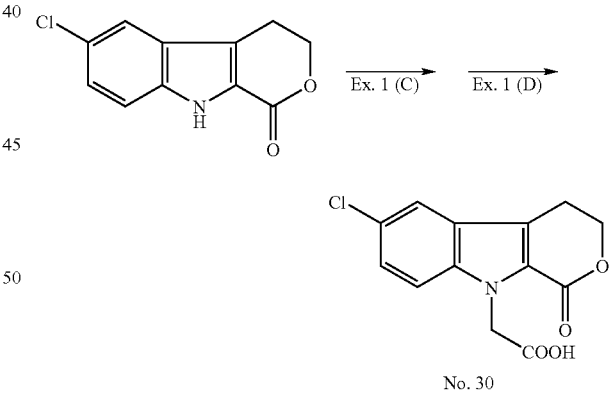

No. 30

The following compound was obtained according to the method described in (C) and (D) of Example 1.

(6-Chloro-1-oxo-3,4-dihydro-1H-pyrano[3,4-b]indol-9-yl)acetic acid (Compound 30)

IR (KBr) 2962, 1715, 1665, 1475, 1288, 1205, 1117, 1105, 771

$^1$H NMR (500 MHz, DMSO-$d_6$) δ 3.15 (2H, t, J=6.4 Hz), 4.61 (2H, t, J=6.4 Hz), 5.26 (2H, s), 7.41 (1H, dd, J=9.0, 2.1 Hz), 7.70 (1H, d, J=9.0 Hz), 7.87 (1H, d, J=2.1 Hz)

Example 3

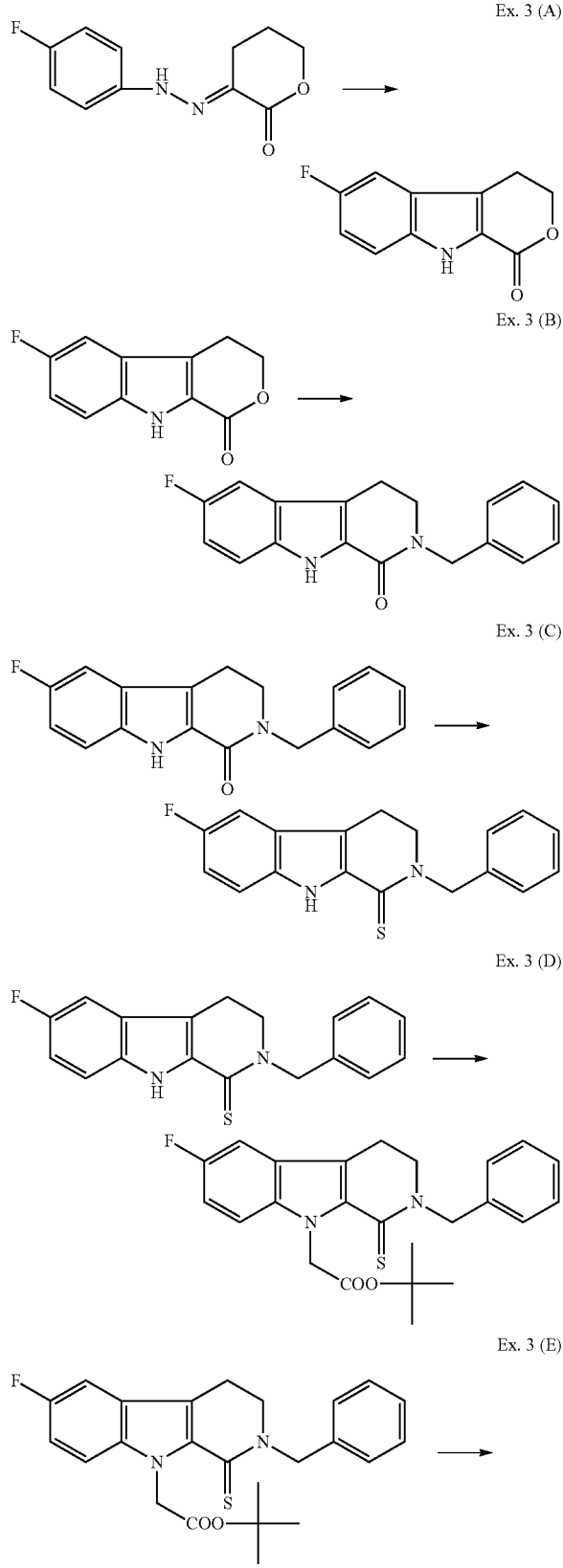

Ex. 3 (A)
Ex. 3 (B)
Ex. 3 (C)
Ex. 3 (D)
Ex. 3 (E)

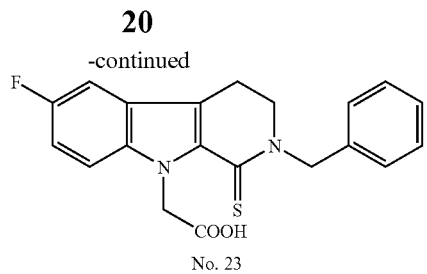

No. 23

(A) A 1 M hydrogen chloride acetic acid solution (40 ml) was added to an acetic acid (40 ml) solution of 3-[(4-fluorophenyl)hydrazono]tetrahydropyran-2-one (14.8 g, 66.8 mmol), followed by heating under reflux for 30 minutes.

After the addition of water (300 ml) to the reaction mixture while cooling with ice, the solid precipitated was collected by filtration, washed with water and hexane, and dried under reduced pressure to obtain
6-fluoro-4,9-dihydro-3H-pyrano[3,4-b]indol-1-one (8.2 g, 60%) as an orange solid.

$^1$H NMR (500 MHz, DMSO-$d_6$) δ 3.08 (2H, t, J=7.2 Hz), 4.62 (2H, t, J=7.2 Hz), 7.20 (1H, t, J=7.8 Hz), 7.42 (1H, m), 7.50 (1H, d, J=7.8 Hz), 12.01 (1H, br).

(B) Benzylamine (0.9 ml, 8.2 mmol) was added to
6-fluoro-4,9-dihydro-3H-pyrano[3,4-b]indol-1-one (1.5 g, 7.3 mmol), followed by heating at 210° C. for three hours.

The reaction mixture was crystallized in ethanol to obtain 2-benzyl-6-fluoro-2,3,4,9-tetrahydro-β-carbolin-1-one (1 g, 49%) as a light yellow solid.

$^1$H NMR (500 MHz, DMSO-$d_6$) δ 2.98 (2H, t, J=7.2 Hz), 3.61 (2H, t, J=7.2 Hz), 4.73 (2H, s), 7.07 (1H, t, J=7.8 Hz), 7.27-7.42 (7H, m), 11.79 (1H, br).

(C) A Lawesson's reagent (434 mg, 1.1 mmol) was added to a toluene (15 ml) solution of 2-benzyl-6-fluoro-2,3,4,9-tetrahydro-β-carbolin-1-one (528 mg, 1.8 mmol), followed by heating under reflux for 14 hours. Then, toluene was evaporated off.

The residue was purified by silica gel column chromatography (silica gel 30 g, eluate: hexane:acetone=20:1) to obtain
2-benzyl-6-fluoro-2,3,4,9-tetrahydro-β-carbolin-1-thione (292 mg, 53%) as a light yellow solid.

mp: 127-130° C.

IR (KBr) 3320, 3060, 3027, 2915, 2898, 1555, 1506, 1465, 1452, 1422, 1338, 1302, 1243, 1170, 804, 695 cm$^{-1}$ $^1$H NMR (500 MHz, DMSO-$d_6$) δ 2.97 (2H, t, J=7.2 Hz), 3.77 (2H, t, J=7.2 Hz), 5.37 (2H, s), 7.11 (1H, td, J=9.4, 2.5 Hz), 7.26-7.41 (6H, m), 7.47 (1H, m), 11.43 (1H, br)

$^{13}$C NMR (75 MHz, DMSO-$d_6$) δ 19.55 (t), 49.60 (t), 55.03 (t), 104.68 & 104.99 (each, d), 111.39 & 111.47 (each, s), 113.13 & 113.49 (each, d), 113.89 & 114.02 (each, d), 124.41 & 124.54 (each, s), 127.26 (d), 127.39 (d), 128.44 (d), 133.75 (s), 135.01 (s), 136.35 (s), 155.30 & 158.39 (each, s), 182.70 (s)

(D) Sodium hydride (60%, 49.8 mg, 1.25 mmol) was added to a dimethyl formamide (5 ml) solution of 2-benzyl-6-fluoro-2,3,4,9-tetrahydro-β-carbolin-1-thione (257 mg, 0.83 mmol), followed by stirring at room temperature for 30 minutes while cooling with ice.

The reaction solution was cooled again to 0° C. and tert-butyl bromoacetate (0.18 ml, 1.25 mmol) was added. After stirring the mixture at room temperature for 16 hours, water (10 ml) was added to terminate the reaction.

The aqueous layer was extracted three times with ether (10 ml). The ether layers were combined. After drying with magnesium sulfate, the ether was evaporated off.

The residue was purified by silica gel column chromatography (silica gel 20 g, eluate: hexane:acetone=20:1) to obtain (2-benzyl-6-fluoro-1-thioxo-1,2,3,4-tetrahydro-(3-carbolin-9-yl)acetic acid tert-butyl ester (328 mg, 93%) as a colorless solid.

mp: 54-56° C.

IR (KBr) 2978, 1742, 1496, 1415, 1368, 1228, 1155, 851, 795, 735 cm⁻¹

$^1$H NMR (500 MHz, CDCl$_3$) δ 1.47 (9H, s), 2.92 (2H, t, J=7.2 Hz), 3.75 (2H, t, J=7.2 Hz), 5.46 (2H, s), 5.71 (2H, br), 7.10 (1H, td, J=9.4, 2.5 Hz), 7.18-7.37 (7H, m)

$^{13}$C NMR (75 MHz, CDCl$_3$) δ 20.22 (t), 27.92 (q), 47.37 (t), 55.31 (t), 81.72 (s), 104.81 & 105.00 (each d), 111.01 & 111.08 (each d), 114.08 & 114.29 (each d), 114.68 & 114.72 (each s), 123.05 & 123.13 (each, s), 127.41 (d), 127.46 (d), 128.49 (d), 133.27 (s), 136.19 (s), 137.07 (s), 157.04 & 158.93 (s), 167.96 (s), 183.17 (s)

(E) A chloroform (2 ml) solution of (2-benzyl-6-fluoro-1-thioxo-1,2,3,4-tetrahydro-β-carbolin-9-yl)acetic acid tert-butyl ester (318 mg, 0.75 mmol) was added to a suspension obtained by adding trimethylsilyl iodide (0.38 ml, 3 mmol) to a chloroform (4 ml) suspension of sodium iodide (450 mg, 3 mmol) and stirring the mixture at room temperature for 30 minutes. The resulting mixture was heated under reflux for three hours.

The aqueous layer was made acidic with 10% hydrochloric acid under cooling with ice and extracted with chloroform (10 ml×6). The chloroform layers were combined. After drying with magnesium sulfate, the chloroform was evaporated off.

The residue was purified by silica gel column chromatography (silica gel: 15 g, eluate: hexane:acetone=20:1 to 3:1) to obtain (2-benzyl-6-fluoro-1-thioxo-1,2,3,4-tetrahydro-β-carbolin-9-yl)acetic acid tert-butyl ester (Compound 23, 235 mg, 85%) as a colorless solid.

mp: 190-191° C.

IR (KBr) 3061, 2925, 1722, 1541, 1496, 1415, 1333, 1246, 1174, 701 cm⁻¹

$^1$H NMR (500 MHz, DMSO-d$_6$) δ 2.97 (2H, t, J=7.2 Hz), 3.76 (2H, t, J=7.2 Hz), 5.43 (2H, s), 5.76 (2H, br), 7.20 (1H, td, J=9.4, 2.5 Hz), 7.30 (1H, m), 7.36 (4H, m), 7.48 (1H, dd, J=9.4, 2.5 Hz), 7.58 (1H, dd, J=9.0, 4.3 Hz)

$^{13}$C NMR (75 MHz, DMSO-d$_6$) δ 19.75 (t), 46.68 (t), 49.53 (t), 54.81 (t), 104.85 & 105.16 (each d), 112.42 & 112.55 (each d), 113.63 & 113.99 (each d), 114.91 & 114.98 (each s), 122.52 & 122.65 (each s), 127.19 (d), 128.41 (d), 132.69 (s), 136.32 & 136.84 (each s), 155.75 (s), 158.86 (s), 170.00 (s), 181.96 (s)

Example 4-1A

Ex.3 (A),(B)

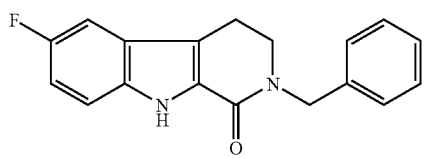
No.22a

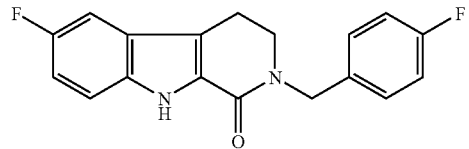
No.25a (A) The following compound was obtained according to the method described in (A) and (B) of Example 3.

2-(2-Fluorophenylmethyl)-6-fluoro-2,3,4,9-tetrahydro-β-carbolin-1-one

Example 4-1B

Ex.3 (D)

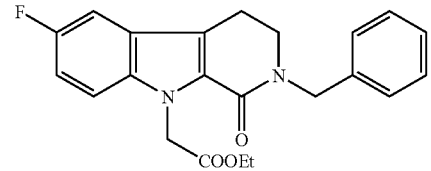
No.22b

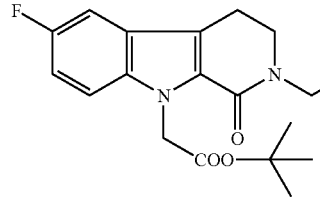
No.25b (B) The following compounds were obtained according to the method described in (D) of Example 3.

(2-Benzyl-6-fluoro-1-oxo-1,2,3,4-tetrahydro-β-carbolin-9-yl)acetic acid ethyl ester

[2-(2-Fluorophenylmethyl)-6-fluoro-1-oxo-1,2,3,4-tetrahydro-β-carbolin-9-yl]acetic acid tert-butyl ester Examples 4-1C Ex.3 (E)

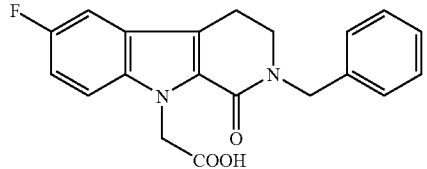
No.22

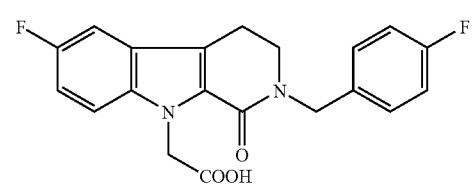
No.25

(C) The following compound was obtained according to the method described in (E) of Example 3.

(2-Benzyl-6-fluoro-1-oxo-1,2,3,4-tetrahydro-β-carbolin-9-yl)acetic acid (Compound 22)

¹H NMR (500 MHz, DMSO-d₆) δ 2.98 (2H, t, J=7.2 Hz), 3.58 (2H, t, J=7.2 Hz), 4.64 (2H, s), 5.38 (2H, s), 7.17 (1H, td, J=9.4, 2.5 Hz), 7.22-7.38 (5H, m), 7.42 (1H, dd, J=9.4, 2.5 Hz), 7.60 (1H, dd, J=9.0, 4.3 Hz)

[2-(2-Fluorophenylmethyl)-6-fluoro-1-oxo-1,2,3,4-tetrahydro-β-carbolin-9-yl]acetic acid (Compound 25)

IR (KBr) 2929, 1724, 1647, 1498, 1247, 1195, 851, 795 cm⁻¹

¹H NMR (500 MHz, DMSO-d₆) δ 2.99 (2H, t, J=7.3 Hz), 3.59 (2H, t, J=7.3 Hz), 4.65 (2H, s), 5.35 (2H, br), 7.14-7.18 (3H, m), 7.33-7.37 (2H, m), 7.43 (1H, dd, J=9.4, 2.6 Hz), 7.59 (1H, dd, J=9.0, 4.2 Hz)

¹³C NMR (75 MHz, DMSO-d₆) δ 19.92 (t), 45.81 (t), 46.99 (t), 47.98 (t), 104.53 & 104.83 (each d), 111.95 & 112.08 (each d), 112.86 & 113.20 (each d), 115.01 & 115.30 (each d), 118.55 (s), 123.71 (s), 126.93 (s), 129.41 & 129.52 (each d), 133.86 (s), 135.27 (s), 155.70 (s), 158.44 (s), 160.25 (s), 170.17 (s)

Example 4-2A

Ex. 3 (A), (B), (C)

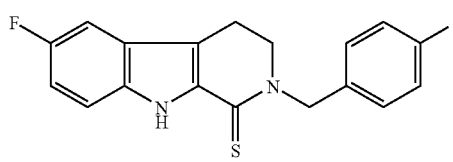
No. 24a

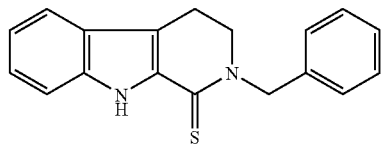
No. 26a

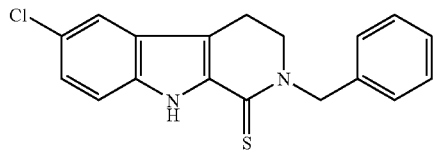
No. 27a

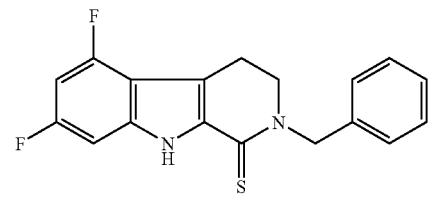
No. 28a

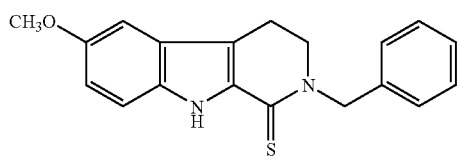
No. 29a

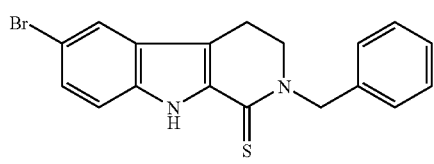
No. 32a

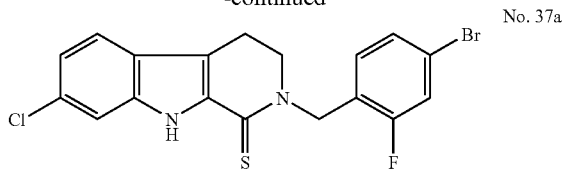
No. 37a

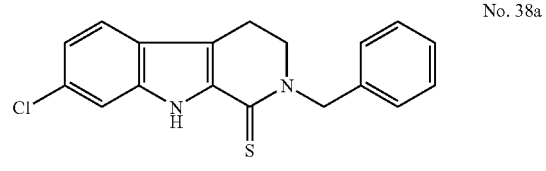
No. 38a

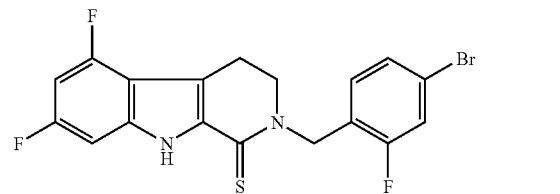
No. 39a

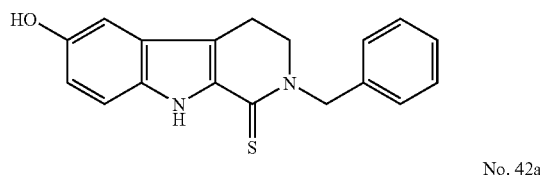
No. 40a

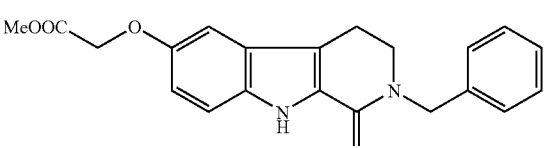
No. 42a

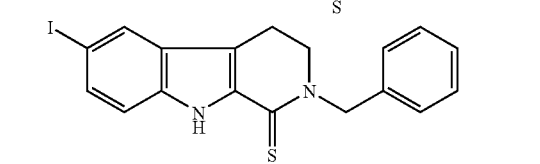

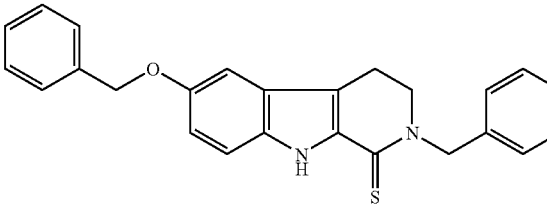

(A) The following compounds were obtained according to the method described in (A) to (C) of Example 3.

2-(4-Fluorophenyl)methyl-6-fluoro-2,3,4,9-tetrahydro-β-carbolin-1-thione (Compound 24a)
mp: 151-152° C.

2-Benzyl-2,3,4,9-tetrahydro-β-carbolin-1-thione (Compound 26a)
mp: 197-198° C.

2-Benzyl-6-chloro-2,3,4,9-tetrahydro-β-carbolin-1-thione (Compound 27a)
¹H NMR (500 MHz, DMSO-d₆) δ 2.99 (2H, t, J=7.3 Hz), 3.78 (2H, t, J=7.3 Hz), 5.37 (2H, s), 7.23 (1H, d, J=9.4 Hz), 7.30 (1H, t, J=9.4 Hz), 7.31-7.40 (4H, brm), 7.49 (1H, d, J=9.4 Hz), 7.69 (1H, s), 11.53 (1H, brs)

2-Benzyl-5,7-difluoro-2,3,4,9-tetrahydro-β-carbolin-1-thione (Compound 28a)

$^1$H NMR (300 MHz, DMSO-$d_6$) δ 2.98 (2H, t, J=7.2 Hz), 3.79 (2H, t, J=7.2 Hz), 5.38 (2H, s), 6.98-7.62 (7H, brm), 11.83 (1H, brs)

2-Benzyl-6-methoxy-2,3,4,9-tetrahydro-β-carbolin-1-thione (Compound 29a)

mp: 173-174° C.

2-Benzyl-6-bromo-2,3,4,9-tetrahydro-β-carbolin-1-thione (Compound 32a)

$^1$H NMR (500 MHz, DMSO-$d_6$) δ 2.98 (2H, t, J=7.2 Hz), 3.76 (2H, t, J=7.2 Hz), 5.36 (2H, s), 7.27-7.47 (7H, brm), 7.82 (1H, s), 11.94 (1H, brs)

2-(2-Fluoro-4-bromophenyl)methyl-7-chloro-2,3,4,9-tetrahydro-β-carbolin-1-thione (Compound 37a)

$^1$H NMR (500 MHz, DMSO-$d_6$) δ 3.06 (2H, t, J=7.1 Hz), 3.79 (2H, t, J=7.1 Hz), 5.34 (2H, s), 6.97-7.67 (6H, brm), 11.45 (1H, brs)

2-Benzyl-7-chloro-2,3,4,9-tetrahydro-β-carbolin-1-thione (Compound 38a)

$^1$H NMR (300 MHz, DMSO-$d_6$) δ 3.00 (2H, t, J=6.9 Hz), 3.79 (2H, t, J=6.9 Hz), 5.37 (2H, s), 7.06 (2H, d-like, J=6.6 Hz), 7.30-7.62 (6H, brm), 11.45 (1H, brs)

2-(2-Fluoro-4-bromophenyl)methyl-5,7-difluoro-2,3,4,9-tetrahydro-β-carbolin-1-thione (Compound 39a)

$^1$H NMR (500 MHz, DMSO-$d_6$) δ 3.14 (2H, t, J=7.2 Hz), 3.87 (2H, t, J=7.2 Hz), 5.33 (2H, s), 6.90 (2H, t, J=8.0 Hz), 7.05 (1H, d, J=8.0 Hz), 7.33 (1H, t, J=8.0 Hz), 7.41 (1H, d, J=8.0 Hz), 11.72 (1H, brs)

2-Benzyl-6-hydroxy-2,3,4,9-tetrahydro-β-carbolin-1-thione (Compound 40a)

$^1$H NMR (500 MHz, DMSO-$d_6$) δ 2.93 (2H, t, J=7.1 Hz), 3.75 (2H, t, J=7.1 Hz), 5.42 (2H, s), 6.80 (1H, d, J=7.8 Hz), 6.83 (1H, s), 7.29-7.44 (6H, m), 8.92 (1H, s), 11.03 (1H, brs)

2-Benzyl-6-hydroxy-2,3,4,9-tetrahydro-β-carbolin-1-thione (Compound 42a)

$^1$H NMR (500 MHz, DMSO-$d_6$) δ 2.93 (2H, t, J=7.1 Hz), 3.75 (2H, t, J=7.1 Hz), 5.42 (2H, s), 6.80 (1H, d, J=7.8 Hz), 6.83 (1H, s), 7.29-7.44 (6H, m), 8.92 (1H, s), 11.03 (1H, brs)

2-Benzyl-6-iodo-2,3,4,9-tetrahydro-β-carbolin-1-thione $^1$H NMR (500 MHz, CDCl$_3$) δ 2.97 (2H, t, J=7.7 Hz), 3.76 (2H, t, J=7.7 Hz), 5.39 (2H, s), 7.20-7.44 (7H, brm), 7.54 (1H, d, J=8.5 Hz), 9.12 (1H, brs)

Example 4-2B

Ex. 3 (D)

No. 24b

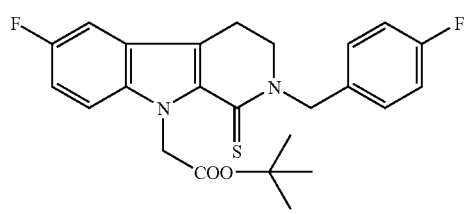

No. 26b

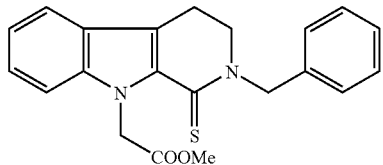

No. 27b

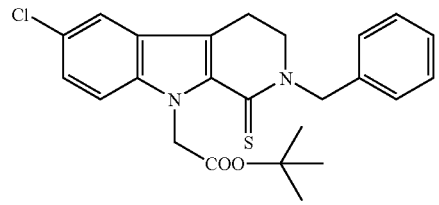

No. 28b

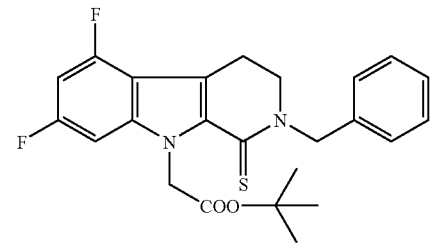

No. 29b

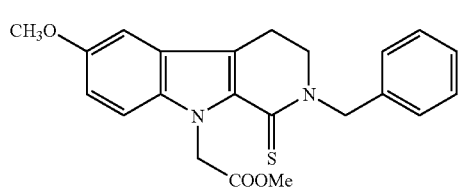

No. 32b

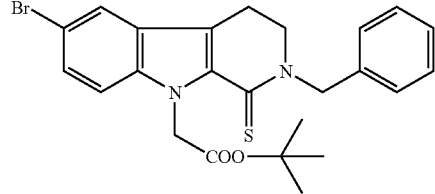

No. 37b

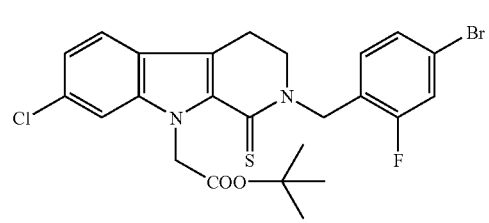

No. 38b

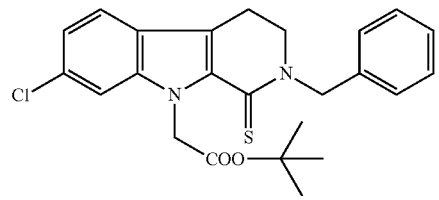

No. 39b

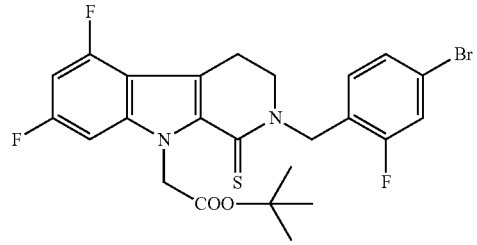

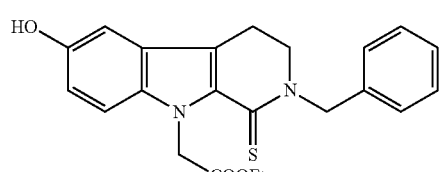
No. 40b

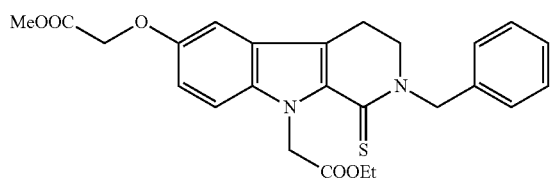
No. 42b (B) The following compounds were obtained according to the method described in (D) of Example 3.

[2-(4-Fluorophenyl)methyl-6-fluoro-1-thioxo-1,2,3,4-tetrahydro-β-carbolin-9-yl]acetic acid tert-butyl ester (Compound 24b)
mp: 54-56° C.

(2-Benzyl-1-thioxo-1,2,3,4-tetrahydro-β-carbolin-9-yl)acetic acid methyl ester (Compound 26b)
$^1$H NMR (500 MHz, CDCl$_3$) δ 2.97 (2H, t, J=7.3 Hz), 3.76 (2H, t, J=7.3 Hz), 3.77 (3H, s), 5.46 (2H, s), 5.86 (2H, brs), 7.18 (1H, t, J=7.7 Hz), 7.27-7.38 (7H, brm), 7.58 (1H, d, J=7.7 Hz)

(2-Benzyl-6-chloro-1-thioxo-1,2,3,4-tetrahydro-β-carbolin-9-yl)acetic acid tert-butyl ester (Compound 27b)
mp: 34-35° C.

(2-Benzyl-5,7-difluoro-1-thioxo-1,2,3,4-tetrahydro-β-carbolin-9-yl)acetic acid tert-butyl ester (Compound 28b)
mp: 63-64° C.

(2-Benzyl-6-methoxy-1-thioxo-1,2,3,4-tetrahydro-β-carbolin-9-yl)acetic acid tert-butyl ester (Compound 29b1)
mp: 44-45° C.

(2-Benzyl-6-methoxy-1-thioxo-1,2,3,4-tetrahydro-β-carbolin-9-yl)acetic acid methyl ester (Compound 29b2)
$^1$H NMR (300 MHz, CDCl$_3$) δ 2.93 (2H, t, J=7.2 Hz), 3.75 (2H, t, J=7.2 Hz), 3.76 (3H, s), 3.84 (3H, s), 5.45 (2H, s), 5.83 (2H, brs), 6.93-7.37 (8H, brm)

(2-Benzyl-6-bromo-1-thioxo-1,2,3,4-tetrahydro-β-carbolin-9-yl)acetic acid tert-butyl ester (Compound 32b)
$^1$H NMR (500 MHz, CDCl$_3$) δ 1.47 & 1.55 (each, s, 9H), 2.92 (2H, t, J=7.2 Hz), 3.74 (2H, t, J=7.2 Hz), 5.45 (2H, s), 5.70 (2H, brs), 7.15 (1H, d, J=8.7 Hz), 7.31-7.43 (6H, brm), 7.69 (1H, s)

[2-(2-Fluoro-4-bromophenyl)methyl-7-chloro-1-thioxo-1,2,3,4-tetrahydro-β-carbolin-9-yl]acetic acid tert-butyl ester (Compound 37b)
$^1$H NMR (500 MHz, CDCl$_3$) δ 1.48 & 1.56 (each, s, 9H), 3.03 (2H, t, J=7.4 Hz), 3.82 (2H, t, J=7.4 Hz), 5.38 (2H, s), 5.43 & 5.61 (2H, each brs), 7.01 (1H, d, J=8.5 Hz), 7.28-7.49 (5H, brm)

(2-Benzyl-7-chloro-1-thioxo-1,2,3,4-tetrahydro-β-carbolin-9-yl)acetic acid tert-butyl ester (Compound 38b)
$^1$H NMR (500 MHz, CDCl$_3$) δ 1.47 & 1.56 (each, s, 9H), 2.94 (2H, t, J=7.3 Hz), 3.74 (2H, t, J=7.3 Hz), 5.46 (2H, s), 5.66 (2H, brs), 7.12 (1H, d-like, J=8.7 Hz), 7.29-7.46 (7H, brm)

[2-(2-Fluoro-4-bromophenyl)methyl-5,7-difluoro-1-thioxo-1,2,3,4-tetrahydro-β-carbolin-9-yl]acetic acid tert-butyl ester (Compound 39b)

$^1$H NMR (500 MHz, CDCl$_3$) δ 1.49 & 1.55 (each, s, 9H), 3.13 (2H, t, J=7.3 Hz), 3.78 (2H, t, J=7.3 Hz), 5.41 (2H, s), 5.58 (2H, brs), 6.62 (1H, dd, J=8.1, 1.7 Hz), 6.74 (1H, d, J=8.1 Hz), 7.24 (1H, d, J=8.1 Hz), 7.27 (1H, d, J=8.1 Hz), 7.35 (1H, t, J=8.1 Hz)

(2-Benzyl-6-hydroxy-1-thioxo-1,2,3,4-tetrahydro-β-carbolin-9-yl)acetic acid ethyl ester (Compound 40b)
$^1$H NMR (500 MHz, CDCl$_3$) δ 1.29 (3H, t, J=7.3 Hz), 2.86 (2H, br), 3.73 (2H, t, J=7.2 Hz), 4.23 (2H, q, J=7.3 Hz), 4.85 (1H, br), 5.44 (2H, s), 5.79 (2H, brs), 6.91 (2H, br), 7.12 (1H, d-like, J=8.9 Hz), 7.29-7.38 (5H, brm)

(2-Benzyl-6-(metoxycarbonylmethoxy)-1-thioxo-1,2,3,4-tetrahydro-β-carbolin-9-yl)acetic acid ethyl ester (Compound 42b)
$^1$H NMR (500 MHz, CDCl$_3$) δ 1.29 (3H, t, J=7.3 Hz), 2.91 (2H, t, J=7.2 Hz), 3.74 (2H, t, J=7.2 Hz), 3.81 (3H, s), 4.23 (2H, q, J=7.3 Hz), 4.67 (2H, s), 5.45 (2H, s), 5.80 (2H, brs), 6.94 (1H, d, J=2.6 Hz), 7.11 (1H, dd, J=9.4, 2.6 Hz), 7.19 (1H, d, J=9.4 Hz), 7.30-7.36 (5H, brm)

(2-Benzyl-6-benzyloxy-1-thioxo-1,2,3,4-tetrahydro-β-carbolin-9-yl)acetic acid tert-butyl ester
$^1$H NMR (500 MHz, CDCl$_3$) δ 1.47 & 1.55 (each, s, 9H), 2.91 (2H, t, J=7.2 Hz), 3.73 (2H, t, J=7.2 Hz), 5.09 (2H, s), 5.46 (2H, s), 5.69 (2H, brs), 7.02 (1H, s-like), 7.11 (1H, d-like, J=8.7 Hz), 7.19 (1H, d-like, J=8.7 Hz), 7.29-7.46 (7H, brm), 7.69 (1H, s) (2-Benzyl-6-iodo-1-thioxo-1,2,3,4-tetrahydro-β-carbolin-9-yl)acetic acid methyl ester
$^1$H NMR (500 MHz, CDCl$_3$) δ 2.92 (2H, t, J=6.9 Hz), 3.74 (2H, t, J=6.9 Hz), 3.77 (3H, s), 5.44 (2H, s), 5.83 (2H, brs), 7.04 (1H, d, J=9.0 Hz), 7.31-7.36 (5H, brm), 7.58 (1H, d, J=9.0 Hz), 7.92 (1H, s)

(2-Benzyl-6-methoxcarbonyl-1-thioxo-1,2,3,4-tetrahydro-β-carbolin-9-yl)acetic acid methyl ester
$^1$H NMR (500 MHz, CDCl$_3$) δ 3.15 (2H, t, J=7.2 Hz), 3.78 (2H, t, J=7.2 Hz), 3.78 (3H, s), 3.94 (3H, s), 5.45 (2H, s), 5.87 (2H, brs), 7.27-7.37 (6H, brm), 8.02 (1H, dd, J=9.0, 1.3 Hz), 8.36 (1H, d, J=1.3 Hz)

Examples 4-2C

Ex. 3 (E)

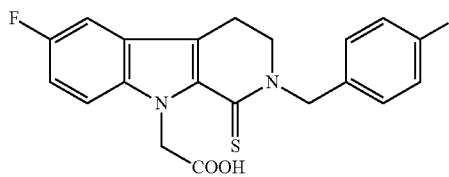
No. 24

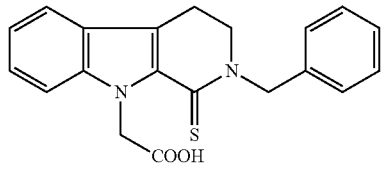
No. 26

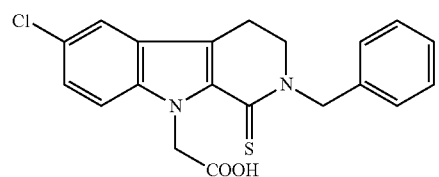
No. 27

-continued

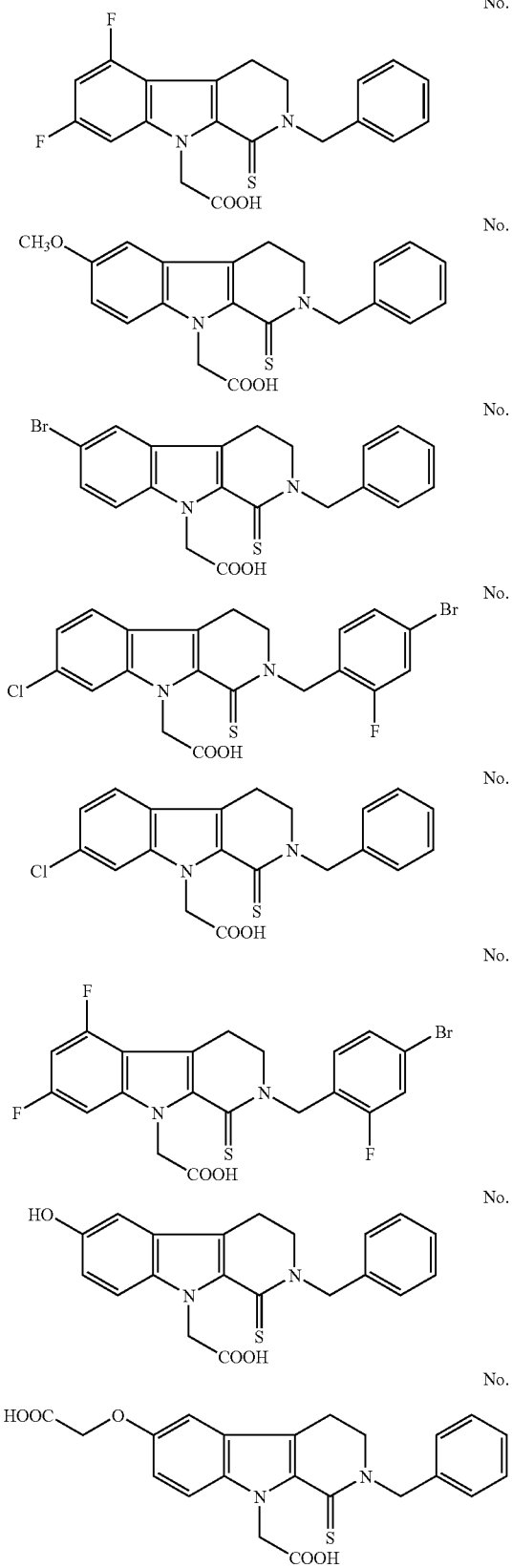

(C) The following compounds were obtained according to the method described in (E) of Example 3.

[2-(2-Fluorophenylmethyl)-6-fluoro-1-thioxo-1,2,3,4-tetrahydro-β-carbolin-9-yl]acetic acid (Compound 24)

mp: 201-202° C.

IR (KBr) 2932, 1731, 1509, 1496, 1332, 1246, 1223, 1175, 852 cm$^{-1}$ $^1$H NMR (500 MHz, DMSO-d$_6$) δ 2.96 (2H, t, J=7.2 Hz), 3.76 (2H, t, J=7.2 Hz), 5.40 (2H, s), 5.75 (2H, br), 7.12-7.25 (3H, m), 7.37-7.48 (3H, m), 7.57 (1H, dd, J=9.1, 4.2 Hz)

$^{13}$C NMR (75 MHz, DMSO-d$_6$) δ 19.73 (t), 46.70 (t), 49.47 (t), 54.05 (t), 104.85 & 105.17 (eachd), 112.44 & 112.55 (eachd), 114.04 & 114.96 (eachd), 115.07 & 115.35 (eachd), 122.48 & 122.63 (each, s), 129.30 & 129.41 (eachd), 132.56 & 132.66 (each, s), 136.85 (s), 155.75 (s), 158.87 (s), 159.63 (s), 170.00 (s), 181.96 (s)

(2-Benzyl-1-thioxo-1,2,3,4-tetrahydro-β-carbolin-9-yl)acetic acid (Compound 26)

mp: 207-209° C.

IR (KBr) 3052, 2924, 1722, 1542, 1495, 1332, 1284, 1244, 742, 700 cm$^{-1}$ $^1$H NMR (500 MHz, DMSO-d$_6$) δ 2.99 (2H, t, J=7.2 Hz), 3.76 (2H, t, J=7.2 Hz), 5.43 (2H, s), 5.77 (2H, br), 7.15 (1H, t, J=7.5 Hz), 7.28-7.37 (6H, m), 7.52 (1H, d, J=7.5 Hz), 7.66 (1H, d, J=7.5 Hz)

$^{13}$C NMR (75 MHz, DMSO-d$_6$) δ 19.81 (t), 46.49 (t), 49.48 (t), 54.71 (t), 110.90 (d), 115.17 (s), 120.54 & 120.69 (eachd), 122.48 (s), 125.24 (d), 127.19 (d), 128.41 (d), 131.51 (s), 136.46 (s), 140.17 (s), 170.12 (s), 182.14 (s)

(2-Benzyl-6-chloro-1-thioxo-1,2,3,4-tetrahydro-β-carbolin-9-yl)acetic acid (Compound 27)

mp: 228-229° C.

IR (KBr) 2360, 1728, 1541, 1487, 1411, 1335, 1296, 1247, 1227, 1078 cm$^{-1}$ $^1$H NMR (500 MHz, DMSO-d$_6$) δ 2.98 (2H, t, J=7.3 Hz), 3.76 (2H, t, J=7.3 Hz), 5.42 (2H, s), 5.76 (2H, br), 7.28-7.38 (6H, m), 7.59 (1H, d, J=9.0 Hz), 7.77 (1H, s)

$^{13}$C NMR (75 MHz, DMSO-d$_6$) δ 19.63 (t), 46.68 (t), 49.52 (t), 54.81 (t), 112.78 (d), 114.57 (s), 119.85 (d), 122.48 (s), 123.50 (s), 124.96 (s), 125.07 (d), 127.23 (d), 128.42 (d), 132.44 (s), 136.29 (s), 138.52 (s), 169.91 (s), 181.88 (s)

(2-Benzyl-5,7-difluoro-1-thioxo-1,2,3,4-tetrahydro-β-carbolin-9-yl)acetic acid (Compound 28)

mp: 219-220° C.

IR (KBr) 2922, 1709, 1642, 1580, 1540, 1479, 1260, 1208, 1094, 829, 702 cm$^{-1}$ $^1$H NMR (500 MHz, DMSO-d$_6$) δ 3.08 (2H, t, J=7.3 Hz), 3.76 (2H, t, J=7.3 Hz), 5.41 (2H, s), 5.71 (2H, br), 6.99 (1H, t, J=10.2 Hz), 7.26-7.36 (5H, m), 7.41 (1H, d, J=10.2 Hz)

(2-Benzyl-6-methoxy-1-thioxo-1,2,3,4-tetrahydro-β-carbolin-9-yl)acetic acid (Compound 29)

IR (KBr) 2937, 1711, 1496, 1328, 1220, 1172, 1047, 797, 736 cm$^{-1}$ $^1$H NMR (500 MHz, DMSO-d$_6$) δ 2.96 (2H, t, J=7.3 Hz), 3.74 (2H, t, J=7.3 Hz), 3.78 (3H, s), 5.42 (2H, s), 5.73 (2H, br), 6.98 (1H, dd, J=9.0, 2.6 Hz), 7.12 (1H, d, J=2.6 Hz), 7.27-7.34 (1H, m), 7.35 (4H, m), 7.44 (1H, d, J=9.0 Hz), $^{13}$C NMR (75 MHz, DMSO-d$_6$) δ 19.91 (t), 46.55 (t), 49.55 (t), 54.69 & 54.89 (eacht), 55.40 (q), 100.90 (d), 111.95 (d), 114.77 (s), 116.47 (d), 122.68 (s), 127.16 & 127.23 (eachd), 128.42 (d), 131.85 (s), 135.67 (s), 136.53 (s), 154.18 (s), 170.18 (s), 182.11 (s)

(2-Benzyl-6-bromo-1-thioxo-1,2,3,4-tetrahydro-β-carbolin-9-yl)acetic acid (Compound 32)

IR (KBr) 2918, 1727, 1538, 1486, 1453, 1409, 1333, 1295, 1248, 1160, 793, 736, 700 cm$^{-1}$ $^1$H NMR (500 MHz, DMSO-d$_6$) δ 2.98 (2H, t, J=7.2 Hz), 3.75 (2H, t, J=7.2 Hz), 5.42 (2H, s), 5.76 (2H, br), 7.27-7.32

(1H, m), 7.36 (4H, m), 7.43 (1H, dd, J=9.0, 2.1 Hz), 7.54 (1H, d, J=9.0 Hz), 7.91 (1H, d, J=2.1 Hz)

$^{13}$C NMR (75 MHz, DMSO-d$_6$) δ 19.63 (t), 46.67 (t), 49.52 (t), 54.82 (t), 112.84 (s), 113.17 (d), 114.48 (s), 122.97 (d), 124.22 (s), 127.24 (d), 127.57 (d), 132.24 (s), 136.30 (s), 138.76 (s), 169.89 (s), 181.86 (s)

[(2-(2-Fluoro-4-bromophenylmethyl)-7-chloro-1-thioxo-1,2,3,4-tetrahydro-β-carbolin-9-yl)acetic acid (Compound 37)

IR (KBr) 2922, 1717, 1488, 1416, 1335, 1283, 1243, 1176, 1068, 876, 805 cm$^{-1}$ $^1$H NMR (500 MHz, DMSO-d$_6$) δ 3.06 (2H, t, J=7.3 Hz), 3.84 (2H, t, J=7.3 Hz), 5.37 (2H, s), 5.71 (2H, br), 7.18 (1H, dd, J=8.5, 1.7 Hz), 7.25 (1H, t, J=8.5 Hz), 7.38 (1H, dd, J=8.5, 1.7 Hz), 7.59 (1H, dd, J=9.8, 2.1 Hz), 7.70-7.74 (2H, m)

$^{13}$C NMR (75 MHz, DMSO-d$_6$) δ 19.70 (t), 46.73 (t), 49.32 (t), 50.11 (t), 110.97 (d), 115.56 (s), 118.50 (s), 118.83 (d), 121.24 (d), 122.31 (d), 122.66 & 122.84 (each, s), 127.53 (s), 130.12 (d), 132.16 (s), 130.38 (s), 132.10 (d), 140.56 (s), 157.01 (s), 158.24 (s), 169.84 (s), 182.35 (s)

(2-Benzyl-7-chloro-1-thioxo-1,2,3,4-tetrahydro-β-carbolin-9-yl)acetic acid (Compound 38)

IR (KBr) 2921, 1721, 1538, 1483, 1452, 1415, 1334, 1281, 1156, 1069, 922, 806, 736, 699 cm$^{-1}$ $^1$H NMR (500 MHz, DMSO-d$_6$) δ 2.98 (2H, t, J=7.3 Hz), 3.76 (2H, t, J=7.3 Hz), 5.42 (2H, s), 5.74 (2H, br), 7.16 (1H, dd, J=8.5, 1.8 Hz), 7.27-7.32 (1H, m), 7.36 (4H, m), 7.69 (1H, d, J=8.5 Hz), 7.74 (1H, d, J=1.8 Hz)

$^{13}$C NMR (75 MHz, DMSO-d$_6$) δ 19.65 (t), 46.73 (t), 49.42 (t), 54.74 (t), 110.93 (d), 115.22 (s), 121.06 (s), 121.26 (d), 122.21 (d), 127.19 (d), 128.41 (d), 129.96 (s), 132.16 (s), 136.32 (s), 140.48 (s), 169.91 (s), 181.81 (s)

[(2-(2-Fluoro-4-bromophenylmethyl)-5,7-difluoro-1-thioxo-1,2,3,4-tetrahydro-β-carbolin-9-yl)acetic acid (Compound 39)

$^1$H NMR (500 MHz, DMSO-d$_6$) δ 3.15 (2H, t, J=7.2 Hz), 3.85 (2H, t, J=7.2 Hz), 5.36

(2H, s), 5.66 (2H, br), 7.00 (1H, t, J=8.5 Hz), 7.26 (1H, t, J=8.1 Hz), 7.36-7.43 (2H, m), 7.60 (1H, dd, J=8.5, 1.7 Hz)

(2-Benzyl-6-hydroxy-1-thioxo-1,2,3,4-tetrahydro-β-carbolin-9-yl)acetic acid (Compound 40)

IR (KBr) 2924, 1721, 1537, 1496, 1415, 1331, 1208, 1175, 1073, 1042, 801 cm$^{-1}$ $^1$H NMR (500 MHz, DMSO-d$_6$) δ 2.95 (2H, t, J=7.2 Hz), 3.77 (2H, t, J=7.2 Hz), 5.42 (2H, s), 5.66 (2H, br), 6.84-6.88 (2H, m), 7.29-7.36 (6H, m), 9.07 (1H, br)

(2-Benzyl-6-carboxymethoxy-1-thioxo-1,2,3,4-tetrahydro-β-carbolin-9-yl)acetic acid (Compound 42)

$^1$H NMR (500 MHz, DMSO-d$_6$) δ 2.89 (2H, t, J=7.3 Hz), 3.72 (2H, t, J=7.3 Hz), 4.68 (2H, s), 5.42 (2H, s), 5.71 (2H, br), 6.97 (1H, dd, J=9.0, 2.2 Hz), 7.16 (1H, d, J=2.2 Hz), 7.28-7.36 (5H, m), 7.44 (1H, d, J=9.0 Hz), 8.33 (1H, s)

Example 4-3A

Ex3 (A), (B), (C)

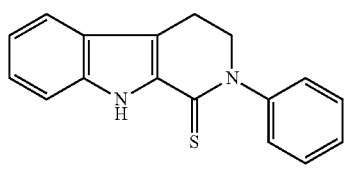

No. 33a

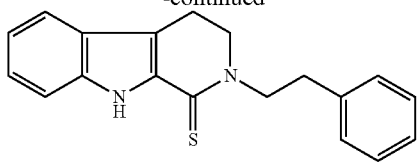

No. 34a

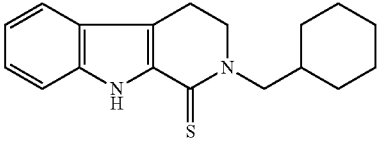

No. 35a

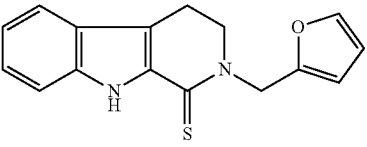

No. 36a

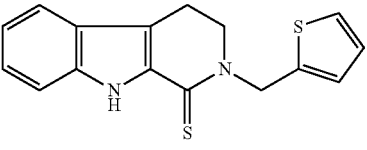

(A) The following compounds were obtained according to the method described in (A) and (B) of Example 3.

2-Phenyl-2,3,4,9-tetrahydro-β-carbolin-1-thione (Compound 33a)

$^1$H NMR (500 MHz, DMSO-d$_6$) δ 3.18 (2H, t, J=7.1 Hz), 4.11 (2H, t, J=7.1 Hz), 6.98-7.67 (9H, brm), 11.31 (1H, brs)

2-Cyclohexylmethyl-2,3,4,9-tetrahydro-β-carbolin-1-thione (Compound 34a)

$^1$H NMR (500 MHz, DMSO-d$_6$) δ 1.05-1.21 (5H, m), 1.61-1.71 (5H, m), 1.96 (1H, m), 3.00 (2H, t, J=7.3 Hz), 3.79 (2H, m), 3.92 (2H, d, J=5.7 Hz), 7.04 (1H, t, J=6.9 Hz), 7.21 (1H, t, J=6.9 Hz), 7.46 (1H, d, J=6.9 Hz), 7.59 (1H, d, J=6.9 Hz), 11.18 (1H, brs)

2-(2-Furylmethyl)-2,3,4,9-tetrahydro-β-carbolin-1-thione (Compound 35a)

$^1$H NMR (500 MHz, DMSO-d$_6$) δ 3.09 (2H, t, J=7.1 Hz), 3.83 (2H, t, J=7.1 Hz), 5.35 (2H, s), 6.45 (2H, m), 7.05 (1H, t, J=7.7 Hz), 7.23 (t, J=7.7 Hz), 7.47 (1H, d, J=7.7 Hz), 7.58 (1H, d, J=8.8 Hz), 7.63 (1H, s), 11.28 (1H, brs)

2-(2-Thienylmethyl)-2,3,4,9-tetrahydro-β-carbolin-1-thione (Compound 36a)

$^1$H NMR (500 MHz, DMSO-d$_6$) δ 2.99 (2H, t, J=6.9 Hz), 3.78 (2H, t, J=6.9 Hz), 6.98-7.62 (7H, brm), 11.31 (1H, brs)

2-Phenetyl-2,3,4,9-tetrahydro-β-carbolin-1-thione

Example 4-3B

Ex3 (D)

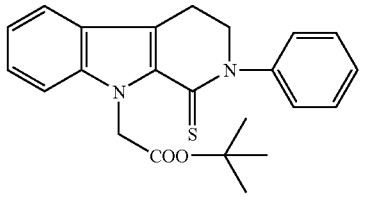

No. 33b

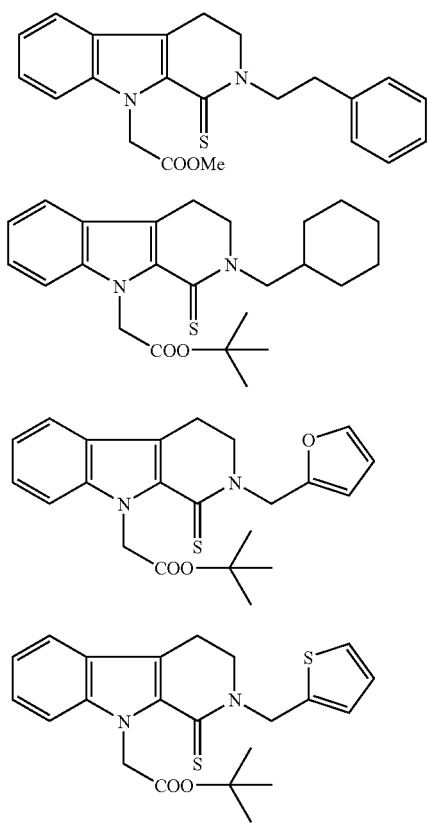

No. 34b

No. 35b

No. 36b (B) The following compounds were obtained according to the method described in (D) of Example 3.

(2-Pheny-1-thioxo-1,2,3,4-tetrahydro-β-carbolin-9-yl)acetic acid tert-butyl ester (33b)

$^1$H NMR (500 MHz, CDCl$_3$) δ 1.45 & 1.56 (each s, 9H), 3.21 (2H, t, J=6.8 Hz), 4.09 (2H, t, J=6.8 Hz), 5.66 (2H, brs), 7.25-7.50 (8H, brm), 7.64 (1H, d, J=7.7 Hz)

(2-Cyclohexylmethyl-1-thioxo-1,2,3,4-tetrahydro-β-carbolin-9-yl)acetic acid t-butyl ester (No. 34b)

$^1$H NMR (500 MHz, CDCl$_3$) δ 1.08-1.25 (5H, m), 1.45 & 1.48 (each, s, 9H), 1.66-1.79 (5H, m), 2.03 (1H, m), 3.01 (2H, t, J=6.8 Hz), 3.78 (2H, t, J=6.8 Hz), 5.69 (2H, brs), 7.12-7.40 (3H, brm), 7.58 (1H, d, J=8.1 Hz)

[2-(2-Furylmethyl)-1-thioxo-1,2,3,4-tetrahydro-β-carbolin-9-yl]acetic acid t-butyl ester (No. 35b)

$^1$H NMR (500 MHz, CDCl$_3$) δ 1.42 & 1.49 (each, s, 9H), 3.02 (2H, t, J=6.8 Hz), 3.83 (2H, t, J=6.8 Hz), 5.41 (2H, s), 5.65 (2H, brs), 6.37 (1H, m), 6.41 (1H, m), 7.16-7.57 (5H, m)

[2-(2-Thienlmethyl)-1-thioxo-1,2,3,4-tetrahydro-β-carbolin-9-yl]acetic acid t-butyl ester (No. 36b)

$^1$H NMR (500 MHz, CDCl$_3$) δ 1.43 & 1.53 (each, s, 9H), 3.00 (2H, t, J=6.8 Hz), 3.82 (2H, t, J=6.8 Hz), 5.56 (2H, s), 5.72 (2H, brs), 6.96-7.55 (7H, m) (2-Phenetyl-1-thioxo-1,2,3,4-tetrahydro-β-carbolin-9-yl)acetic acid methyl ester $^1$H NMR (500 MHz, CDCl$_3$) δ 2.85 (2H, t, J=7.2 Hz), 3.12 (2H, t, J=7.2 Hz), 3.60 (2H, t, J=7.2 Hz), 3.76 (3H, s), 5.85 (2H, s), 7.16 (1H, t, J=7.6 Hz), 7.25-7.35 (7H, brm), 7.56 (1H, d, J=7.6 Hz)

Example 4-3C

Ex3 (E)

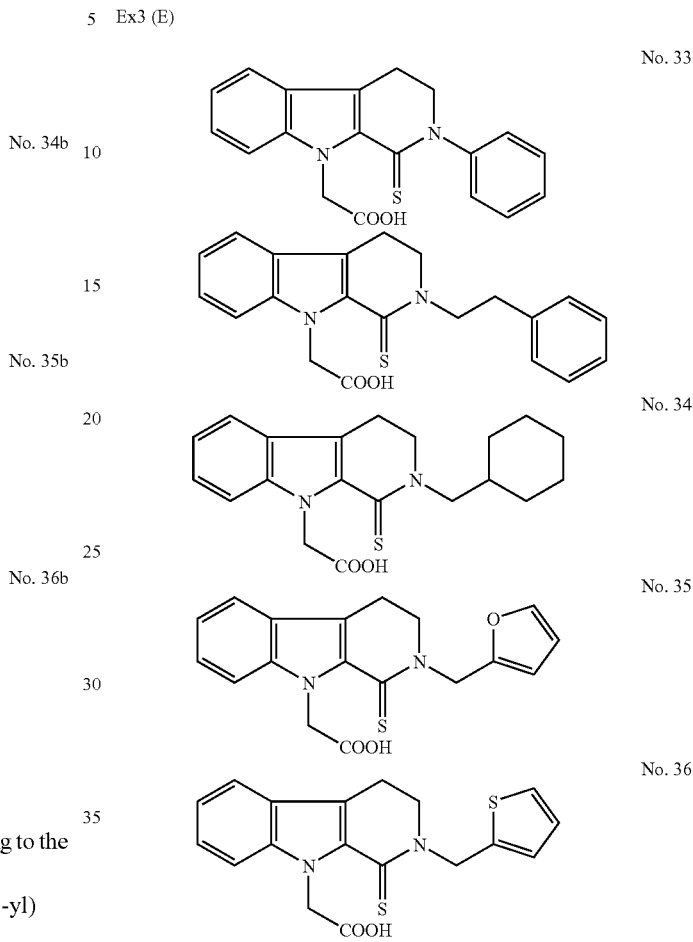

No. 33

No. 34

No. 35

No. 36

(C) The following compounds were obtained according to the method described in (E) of Example 3.

(2-Phenyl-1-thioxo-1,2,3,4-tetrahydro-β-carbolin-9-yl)acetic acid (Compound 33)

IR (KBr) 3047, 2974, 2914, 1772, 1721, 1538, 1493, 1455, 1325, 1278, 1253, 1091, 743, 694 cm$^{-1}$ $^1$H NMR (500 MHz, DMSO-d$_6$) δ 3.20 (2H, t, J=7.3 Hz), 4.04 (2H, t, J=7.3 Hz), 5.75 (2H, s), 7.19 (1H, t, J=7.5 Hz), 7.34-7.38 (4H, m), 7.46-7.53 (3H, m), 7.74 (1H, d, J=7.5 Hz)

$^{13}$C NMR (75 MHz, DMSO-d$_6$) δ 20.34 (t), 46.46 (t), 53.67 (t), 110.95 (d), 115.71 (s), 120.66 (d), 120.90 (d), 122.53 (s), 125.51 (d), 127.14 (d), 129.13 (d), 131.58 (s), 140.28 (s), 146.22 (s), 170.02 (s), 183.38 (s)

(2-Cyclohexylmethyl-1-thioxo-1,2,3,4-tetrahydro-β-carbolin-9-yl)acetic acid (Compound 34)

IR (KBr) 3058, 2921, 1720, 1541, 1487, 1288, 1249, 1214, 1141, 738 cm$^{-1}$ $^1$H NMR (500 MHz, DMSO-d$_6$) δ 1.02-1.20 (5H, m), 1.63-1.70 (5H, m), 1.95 (1H, m), 2.99 (2H, t, J=7.3 Hz), 3.78 (2H, t, J=7.3 Hz), 3.96 (2H, d, J=7.3 Hz), 5.75 (2H, br), 7.14 (1H, t, J=7.5 Hz), 7.31 (1H, t, J=7.5 Hz), 7.47 (1H, d, J=7.5 Hz), 7.66 (1H, d, J=7.5 Hz)

$^{13}$C NMR (75 MHz, DMSO-d$_6$) δ 19.78 (t), 25.49 (t), 26.01 (t), 30.28 (t), 35.96 (d), 46.39 (t), 51.05 (t), 58.35 (t), 110.80 (d), 114.85 (s), 120.46 (d), 120.59 (d), 122.52 (s), 125.03 (d), 131.84 (s), 140.02 (s), 170.10 (s), 181.56 (s)

[2-(2-Furanylmethyl)-1-thioxo-1,2,3,4-tetrahydro-β-carbolin-9-yl]acetic acid (Compound 35)

mp: 195-196° C.

IR (KBr) 3130, 3107, 3067, 2967, 2947, 2856, 2775, 2662, 1710, 1535, 1475, 1435, 1327, 1284, 1251, 1013, 740 cm$^{-1}$ $^1$H NMR (500 MHz, DMSO-d$_6$) δ 3.00 (2H, t, J=7.3 Hz), 3.83 (2H, t, J=7.3 Hz), 5.40 (2H, s), 5.74 (2H, br), 6.44 (2H, m), 7.15 (1H, t, J=7.5 Hz), 7.33 (1H, t, J=7.5 Hz), 7.50 (1H, d, J=7.5 Hz), 7.64 (1H, s), 7.65 (1H, d, J=7.5 Hz)

$^{13}$C NMR (75 MHz, DMSO-d$_6$) δ 19.75 (t), 46.43 (t), 48.02 (t), 49.53 (t), 108.62 (d), 110.45 (d), 110.88 (d), 115.28 (s), 120.54 (d), 120.72 (d), 122.42 (s), 125.28 (d), 131.45 (s), 140.19 (s), 142.58 (d), 149.54 (s), 170.05 (s), 181.90 (s)

[2-(2-Thienylmethyl)-1-thioxo-1,2,3,4-tetrahydro-β-carbolin-9-yl]acetic acid (Compound 36)

mp: 210-212° C.

IR (KBr) 3049, 2920, 1720, 1541, 1484, 1435, 1329, 1287, 1245, 1209, 745, 698 cm$^{-1}$ $^1$H NMR (500 MHz, DMSO-d$_6$) δ 2.97 (2H, t, J=7.3 Hz), 3.82 (2H, t, J=7.3 Hz), 5.54 (2H, s), 5.75 (2H, br), 7.01 (1H, dd, J=5.1, 3.4 Hz), 7.14 (1H, t, J=7.5 Hz), 7.22 (1H, dd, J=3.4, 1.3 Hz), 7.33 (1H, t, J=7.5 Hz), 7.45 (1H, dd, J=5.1, 1.3 Hz), 7.50 (1H, d, J=7.5 Hz), 7.65 (1H, d, J=7.5 Hz)

(2-Phenetyl-1-thioxo-1,2,3,4-tetrahydro-β-carbolin-9-yl)acetic acid $^1$H NMR (500 MHz, DMSO-d$_6$) δ 2.89 (2H, t, J=6.8 Hz), 3.03 (2H, t, J=8.2 Hz), 3.71 (2H, t, J=6.8 Hz), 4.29 (2H, t, J=8.2 Hz), 5.76 (2H, s), 7.15 (1H, t, J=7.6 Hz), 7.30 (1H, m), 7.32 (5H, m), 7.47 (1H, d, J=7.6 Hz), 7.65 (1H, d, J=7.6 Hz)

Example 5

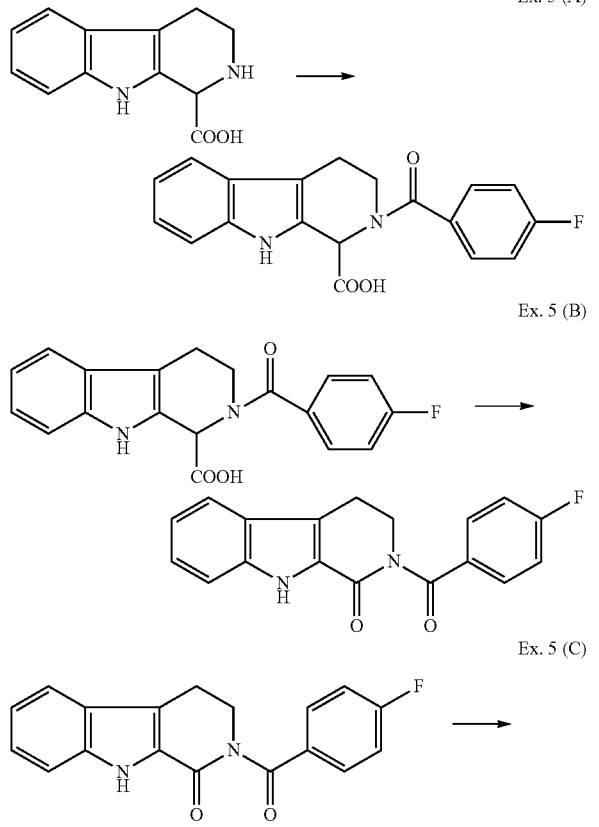

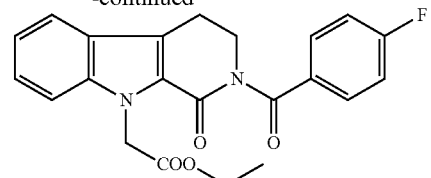

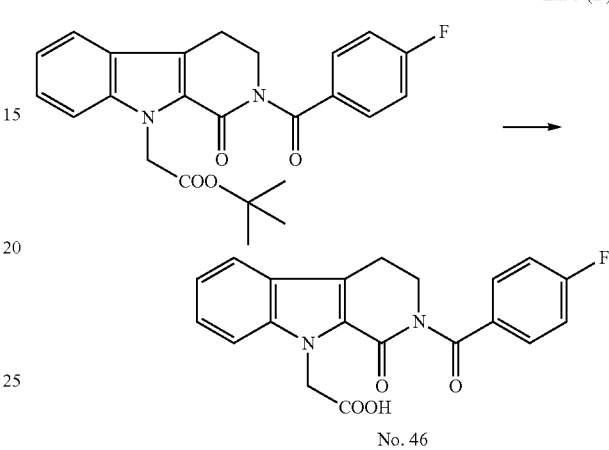

(A) 4-fluorobenzoyl chloride (8 mmol) and a 2N aqueous sodium hydroxide (6.2 ml) were added to a solution of 1,2,3,4-tetrahydro-β-carboline-1-carboxylic acid (8 mmol) in a mixed solvent of 2N aqueous sodium hydroxide (4.2 ml) and dioxane (4.2 ml) followed by stirring at 0° C. for 20 minutes. The reaction mixture was stirred at room temperature for 20 hours.

Then, the reaction mixture was acidified with concentrated hydrochloric acid to obtain a solid material, which was washed with water and dried to obtain a carboxylic acid product.

(B) 1-Ethyl-3-(3-dimethylaminopropyl)carbodiimide hydrochloride (EDC) (403 mg, 2.1 mmol) was added to methylene chloride (10 ml) solution of the resulting carboxylic acid product (2 mmol). The mixture was stirred in an oxygen atmosphere (1 atm) at room temperature for 24 hours.

Acetic acid (0.41 ml) was added to the reaction mixture. The resulting mixture was stirred for 0.5 hours and diluted with methylene chloride. The organic layer was washed with a saturated aqueous solution of sodium hydrogencarbonate, dried with magnesium sulfate, and the solvent was evaporated.

The residue was purified by silica gel column chromatography (eluate: methylene chloride:ethyl acetate=10:1) to obtain 2-(4-Fluorobenzoyl)-1-oxo-1,2,3,4-tetrahydro-β-carboline (yield: 54%).

mp: 255-256° C.

IR (KBr) 3281, 1672 cm$^{-1}$ $^1$H NMR (500 MHz, DMSO-d$_6$) δ 3.21 (2H, t, J=6.4 Hz), 4.21 (2H, t, J=6.4 Hz), 7.13 (1H, t, J=7.7 Hz), 7.25 (2H, t, J=8.5 Hz), 7.32 (1H, t, J=7.7 Hz), 7.42 (1H, d, J=7.7 Hz), 7.66 (2H, m), 7.71 (1H, d, J=7.7 Hz), 11.79 (1H, s)

$^{13}$C NMR (75 MHz, DMSO-d$_6$) δ 20.6 (t), 46.6 (t), 112.7 (d), 114.7 (d), 115.0 (d), 120.0 (d), 120.9 (d), 123.2 (s), 124.2 (s), 125.5 (s), 125.8 (d), 130.7 (d), 130.8 (d), 132.9 (s), 138.4 (s), 160.9 (s), 171.8 (s)

(C) Sodium hydride (60%, 60 mg, 1.5 mmol) was added to a dimethyl formamide (10 ml) solution of 2-(4-Fluorobenzoyl)-1-oxo-1,2,3,4-tetrahydro-β-carboline (1.0 mmol), followed by stirring at room temperature for 30 minutes.

The reaction solution was cooled again to 0° C. and tert-butyl bromoacetate (0.22 ml, 1.5 mmol) was added, followed by stirring at room temperature for 24 hours.

The reaction mixture was diluted with diethyl ether, and the organic layer was washed with water and separated.

The aqueous layer was extracted three times with diethyl ether. The organic layers and the extracts were combined. After drying with magnesium sulfate, the solvent was evaporated off.

The residue was purified by silica gel column chromatography (hexane:acetone=15:1 to 10:1) to obtain t-butyl [2-(4-fluorobenzoyl)-1-oxo-1,2,3,4-tetrahydro-β-carbolin-9-yl]acetate (yield: 80%).

mp: 82-84° C.

IR (KBr) 3056, 1746, 1686 cm$^{-1}$ $^{1}$H NMR (500 MHz, DMSO-d$_6$) δ 1.38 (9H, s), 3.25 (2H, t, J=6.4 Hz), 4.32 (2H, t, J=6.4 Hz), 5.14 (2H, s), 7.04 (2H, t, J=8.5 Hz), 7.20-7.30 (2H, m), 7.43 (1H, t-like, J=8.2 Hz), 7.63-7.70 (3H, m)

$^{13}$C NMR (75 MHz, DMSO-d$_6$) δ 21.3 (t), 27.9 (q), 46.4 (t), 46.5 (t), 82.1 (s), 109.8 (d), 114.8 (d), 115.1 (d), 121.0 (d), 121.1 (d), 123.8 (s), 124.7 (s), 126.7 (d), 130.6 (d), 130.7 (d), 132.2 (s), 140.0 (s), 161.9 (s), 167.5 (s), 172.4 (s)

(D) A chloroform (2 ml) solution of t-butyl[2-(4-fluorobenzoyl)-1-oxo-1,2,3,4-tetrahydro-β-carbolin-9-yl]acetate (0.5 mmol) was added to a trimethylsilyl iodide solution prepared by adding sodium iodide (2.0 mmol) to a chloroform (3 ml) solution of trimethylsilyl chloride (2.0 mmol). The resulting mixture was heated under reflux for 16 hours.

After acidifying the reaction mixture with 10% hydrochloric acid under cooling with ice, the aqueous layer was extracted six times with chloroform (10 ml).

The chloroform layers were combined. After drying with magnesium sulfate, the chloroform was evaporated off.

The residue was purified by silica gel column chromatography (hexane:acetone=20:1 to 2:1) to obtain [2-(4-fluorobenzoyl)-1-oxo-1,2,3,4-tetrahydro-β-carbolin-9-yl]acetic acid (Compound 46, yield 66%).

mp: 240-242° C.

IR (KBr) 3058, 2661, 2571, 1729, 1671 cm$^{-1}$ $^{1}$H NMR (500 MHz, DMSO-d$_6$) δ 3.25 (2H, t, J=6.0 Hz), 4.18 (2H, t, J=6.0 Hz), 5.19 (2H, s), 7.19-7.26 (3H, m), 7.41 (1H, t, J=7.7 Hz), 7.62-7.66 (2H, m), 7.77 (1H, d, J=7.7 Hz)

$^{13}$C NMR (75 MHz, DMSO-d$_6$) δ 20.6 (t), 45.8 (t), 46.4 (t), 110.8 (d), 114.8 (d), 115.1 (d), 120.6 (d), 121.1 (d), 123.3 (s), 124.4 (s), 124.6 (s), 126.3 (d), 130.7 (d), 130.6 (d), 130.7 (d), 132.7 (s), 139.8 (s), 161.4 (s), 169.9 (s), 172.0 (s)

Example 6

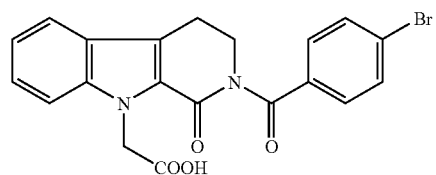

No. 47

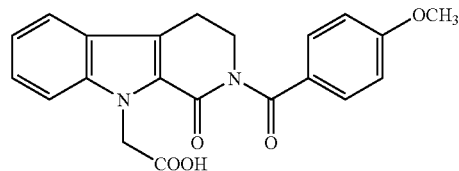

No. 48

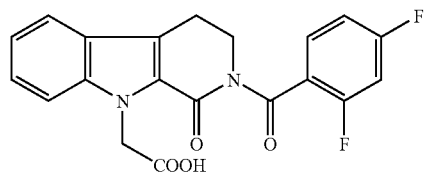

No. 49

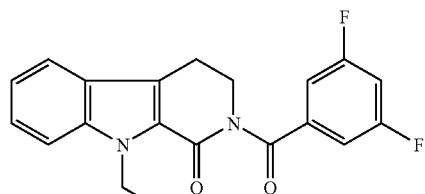

No. 50

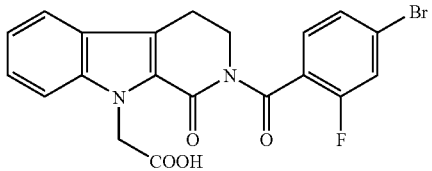

No. 51

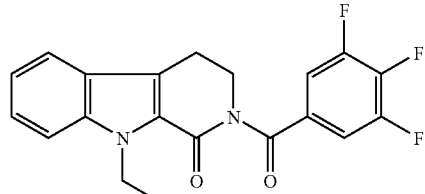

No. 52

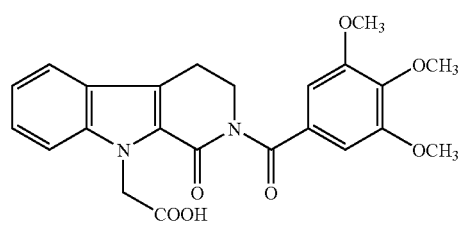

No. 53

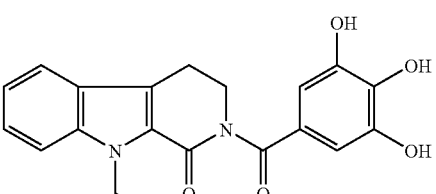

No. 54

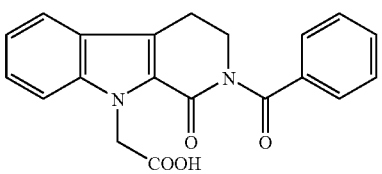

No. 55

The following compound was obtained according to the method described in

Example 5

[2-(4-Bromobenzoyl)-1-oxo-1,2,3,4-tetrahydro-β-carbolin-9-yl]acetic acid (Compound 47)

Yield: 66%, mp: 260-262° C.

IR (KBr) 3054, 2660, 2574, 1726, 1666 cm$^{-1}$ $^1$H NMR (500 MHz, DMSO-d$_6$) δ 3.25 (2H, t, J=6.3 Hz), 4.19 (2H, t, J=6.3 Hz), 5.18 (2H, s), 7.21 (1H, t, J=7.7 Hz), 7.41 (1H, t, J=7.7 Hz), 7.50 (2H, d, J=8.5 Hz), 7.60 (2H, d, J=8.5 Hz), 7.61 (1H, d, J=7.7 Hz), 7.77 (1H, d, J=7.7 Hz)

$^{13}$C NMR (75 MHz, DMSO-d$_6$) δ 20.6 (t), 45.8 (t), 46.2 (t), 110.8 (d), 120.6 (d), 121.1 (d), 123.3 (s), 124.3 (s), 124.7 (s), 124.8 (s), 126.4 (s), 129.8 (d), 130.9 (d), 135.5 (s), 139.8 (s), 161.3 (s), 169.9 (s), 172.0 (s)

[2-(4-Methoxybenzoyl))-1-oxo-1,2,3,4-tetrahydro-β-carbolin-9-yl]acetic acid (Compound 48)

Yield: 73%, mp: 235-236° C.

IR (KBr) 3076, 2662, 2571, 1707, 1667 cm$^{-1}$ $^1$H NMR (500 MHz, DMSO-d$_6$) δ 3.22 (2H, t, J=6.4 Hz), 3.82 (3H, s), 4.13 (2H, t, J=6.4 Hz), 5.20 (2H, s), 6.95 (2H, d, J=8.6 Hz), 7.20 (1H, t, J=7.7 Hz), 7.40 (1H, t, J=7.7 Hz), 7.62 (1H, d, J=7.7 Hz), 7.56 (2H, d, J=8.6 Hz), 7.75 (1H, d, J=7.7 Hz)

$^{13}$C NMR (75 MHz, DMSO-d$_6$) δ 20.7 (t), 45.8 (t), 46.7 (t), 55.4 (q), 110.8 (d), 113.2 (d), 120.6 (d), 121.0 (d), 123.3 (s), 124.2 (s), 124.6 (s), 126.2 (d), 128.0 (s), 130.5 (d), 139.7 (s), 161.6 (s), 161.8 (s), 170.0 (s), 172.6 (s)

[2-(2,4-Difluorobenzoyl)-1-oxo-1,2,3,4-tetrahydro-β-carbolin-9-yl]acetic acid (Compound 49)

Yield: 60%, mp: 237-239° C.

IR (KBr) 3056, 2661, 2575, 1711, 1681 cm$^{-1}$ $^1$H NMR (500 MHz, DMSO-d$_6$) δ 3.21 (2H, t, J=6.4 Hz), 4.27 (2H, t, J=6.4 Hz), 5.18 (2H, s), 7.12-7.31 (3H, m), 7.41 (1H, t, J=7.4 Hz), 7.61 (2H, ABq-like, J=15.4 Hz), 7.76 (1H, d, J=7.4 Hz)

$^{13}$C NMR (75 MHz, DMSO-d$_6$) δ 20.5 (t), 45.3 (t), 45.7 (t), 104.1 (d), 110.9 (d), 111.4 (d), 111.7 (d), 120.7 (d), 121.1 (d), 123.2 (s), 124.1 (s), 125.1 (s), 126.5 (d), 130.8 (d), 139.9 (s), 160.6 (s), 166.2 (s), 169.7 (s)

[2-(3,5-Difluorobenzoyl)-1-oxo-1,2,3,4-tetrahydro-β-carbolin-9-yl]acetic acid (Compound 50)

Yield: 70%, mp: 240-241° C.

IR (KBr) 3057, 2661, 2573, 1713, 1679 cm$^{-1}$ $^1$H NMR (500 MHz, DMSO-d$_6$) δ 3.27 (2H, t, J=6.4 Hz), 4.20 (2H, t, J=6.4 Hz), 5.18 (2H, s), 7.21 (1H, t, J=7.7 Hz), 7.28 (2H, d-like, J=6.8 Hz), 7.41 (2H, m), 7.62 (1H, d, J=7.7 Hz), 7.77 (1H, m), 7.71 (1H, d, J=7.7 Hz), 7.76 (1H, m), 11.84 (1H, s)

$^{13}$C NMR (75 MHz, DMSO-d$_6$) δ 20.4 (t), 45.8 (t), 46.1 (t), 106.1 (d), 110.6 (d), 110.9 (d), 111.0 (d), 120.7 (d), 121.1 (d), 123.2 (s), 124.1 (s), 125.2 (s), 126.5 (d), 139.9 (s), 140.2 (s), 160.1 (s), 160.9 (s), 169.9 (s), 170.4 (s)

[2-(2-Fluoro-4-bromobenzoyl)-1-oxo-1,2,3,4-tetrahydro-β-carbolin-9-yl]acetic acid (Compound 51)

$^1$H NMR (500 MHz, DMSO-d$_6$) δ 3.21 (2H, t, J=6.4 Hz), 4.28 (2H, t, J=6.4 Hz), 5.17 (2H, s), 7.21 (1H, t, J=8.1 Hz), 7.41 (1H, t, J=8.1 Hz), 7.49 (2H, m), 7.58 (1H, d, J=8.1 Hz), 7.61 (1H, d, J=8.1 Hz), 7.76 (1H, d, J=8.1 Hz)

[2-(3,4,5-Trifluorobenzoyl)-1-oxo-1,2,3,4-tetrahydro-β-carbolin-9-yl]acetic acid (Compound 52)

$^1$H NMR (300 MHz, DMSO-d$_6$) δ 3.22 (2H, t, J=6.0 Hz), 4.27 (2H, t, J=6.0 Hz), 5.18 (2H, s), 7.21 (1H, t, J=7.1 Hz), 7.41 (1H, t, J=7.1 Hz), 7.55-7.78 (4H, m)

[2-(3,4,5-Trimetoxybenzoyl)-1-oxo-1,2,3,4-tetrahydro-β-carbolin-9-yl]acetic acid (Compound 53)

$^1$H NMR (500 MHz, DMSO-d$_6$) δ 3.25 (2H, t, J=6.0 Hz), 4.16 (2H, t, J=6.0 Hz), 5.20 (2H, s), 6.87 (2H, s), 7.21 (1H, t, J=8.2 Hz), 7.40 (1H, t, J=8.2 Hz), 7.62 (1H, d, J=8.2 Hz), 7.76 (1H, d, J=8.2 Hz)

[2-(3,4,5-Trihydroxybenzoyl)-1-oxo-1,2,3,4-tetrahydro-β-carbolin-9-yl]acetic acid (Compound 54)

$^1$H NMR (500 MHz, DMSO-d$_6$) δ 3.18 (2H, t, J=6.4 Hz), 4.04 (2H, t, J=6.4 Hz), 5.21 (2H, s), 6.63 (2H, s), 7.19 (1H, t, J=8.1 Hz), 7.39 (1H, t, J=8.1 Hz), 7.59 (1H, d, J=8.1 Hz), 7.75 (1H, d, J=8.1 Hz)

(2-Benzoyl-1-oxo-1,2,3,4-tetrahydro-β-carbolin-9-yl)acetic acid (Compound 55)

IR (KBr) 3058, 2937, 1681, 1469, 1320, 1293, 1243, 1138, 1047 cm$^{-1}$

Example 7

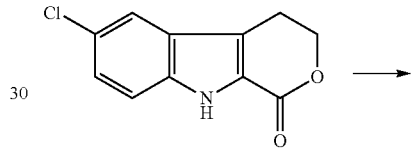

Ex. 7 (A)

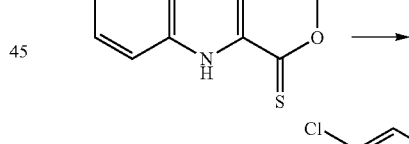

Ex 1 (B)

Ex. 7 (B)

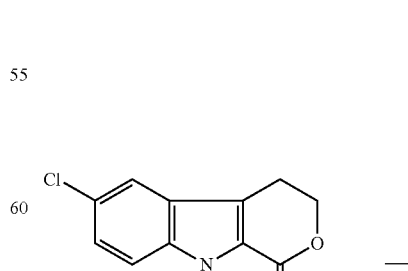

Ex. 1 (C)
No 31a

Ex. 7 (C)

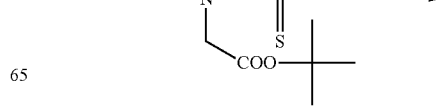

-continued

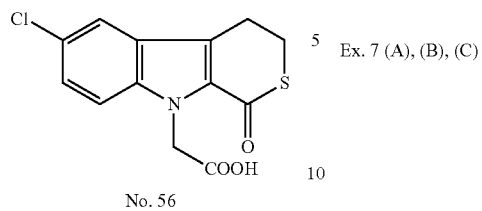

No. 56

(A) A Lawesson's reagent (0.55 Eq) was added to a toluene solution of 6-chloro-4,9-dihydro-3H-pyrano[3,4-b]indol-1-one, followed by heating under reflux for 15 hours. Then, the solvent was evaporated off.

The residue was purified by silica gel column chromatography (eluate: hexane:acetone=20:1) to obtain 6-chloro-4,9-dihydro-3H-pyrano[3,4-b]indole-1-thione (yield: 84%).

$^1$H NMR (500 MHz, CDCl$_3$) δ 3.15 (2H, t, J=6.6 Hz), 4.76 (2H, t, J=6.6 Hz), 7.35 (2H, s), 7.61 (1H, s), 8.88 (1H, br)

(B) Sodium hydride (1.2 eq) was added to a dimethyl formamide solution of 6-chloro-4,9-dihydro-3H-pyrano[3,4-b]indole-1-thione. After stirring for 30 minutes, tert-butyl bromoacetate (1.2 eq) was added and the mixture was stirred at room temperature for 15 hours.

Water and diethyl ether were added to the reaction solution to separate the organic layer. The aqueous layer was extracted three times with diethyl ether.

The organic layer and diethyl ether extracts were combined. After drying with magnesium sulfate, the solvent was evaporated off under reduced pressure.

The residue was purified by silica gel column chromatography (hexane:acetone=20:1 to 15:1) to obtain (6-chloro-1-thioxo-3,4-dihydro-1H-pyrano[3,4-b]indol-9-yl) acetic acid tert-butyl ester (yield: 84%).

$^1$H NMR (500 MHz, CDCl$_3$) δ 1.45 (9H, s), 3.15 (2H, t, J=6.4 Hz), 4.68 (2H, t, J=6.4 Hz), 5.49 (2H, brs), 7.21 (1H, d, J=9.0 Hz), 7.39 (1H, d, J=9.0 Hz), 7.63 (1H, s)

(C) A dichloroethane solution of (6-chloro-1-thioxo-3,4-dihydro-1H-pyrano[3,4-b]indol-9-yl)acetic acid tert-butyl ester was added to a suspension obtained by adding trimethylsilyl chloride (4 Eq) to a dichloroethane suspension of sodium iodide (4 Eq) and stirring at 0° C. for one hour. The resulting mixture was heated under reflux for 48 hours.

The aqueous layer was acidified with 10% hydrochloric acid under cooling with ice and extracted six times with chloroform.

The chloroform layers were combined and dried with magnesium sulfate, after which the chloroform was evaporated off under reduced prerssure.

The residue was purified by silica gel column chromatography (hexane:acetone=3:1 to 2:1) to obtain (6-chloro-1-oxo-3,4-dihydro-1H-2-thia-9-azafluoren-9-yl)acetic acid (Compound 56) (yield: 40%).

IR (KBr) 1727, 1624 cm$^{-1}$ $^1$H NMR (500 MHz, DMSO-d$_6$) δ 2.41 (3H, s), 3.27 (2H, t, J=6.8 Hz), 3.47 (2H, t, J=6.8 Hz), 5.18 (2H, s), 7.25 (1H, d, J=8.5 Hz), 7.50 (1H, t, J=8.5 Hz), 7.54 (1H, s)

Example 8

Ex. 7 (A), (B), (C)

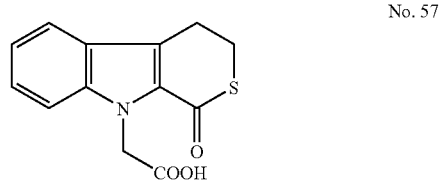

No. 57

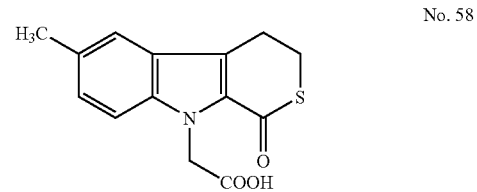

No. 58

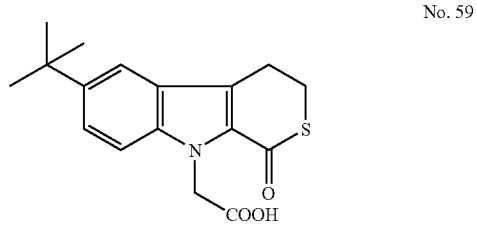

No. 59

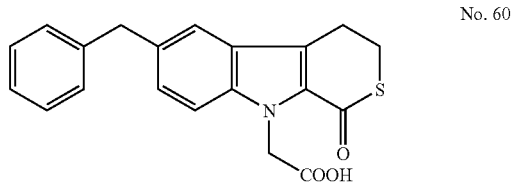

No. 60

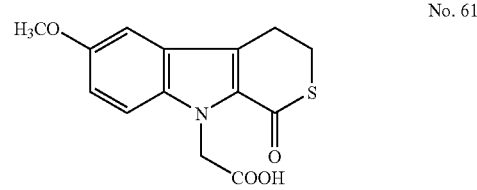

No. 61

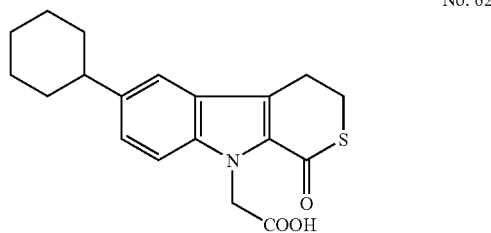

No. 62

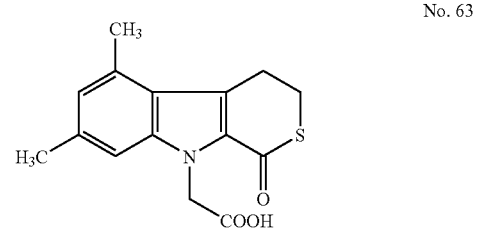

No. 63

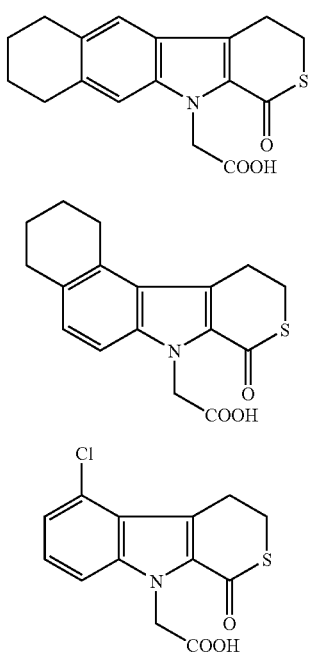

The following compounds were prepared in the same manner as in Example 7.

4,9-dihydro-3H-pyrano[3,4-b]indole-1-thione
Yield: 99%

1-Thioxo-3,4-dihydro-1H-pyrano[3,4-b]indol-9-yl) acetic acid tert-butyl ester

Yield: 92%
$^1$H NMR (300 MHz, CDCl$_3$) δ 1.46 (9H, s), 3.15 (2H, t, J=6.4 Hz), 4.61 (2H, t, J=6.4 Hz), 5.47 (2H, brs), 7.18 (1H, t, J=8.7 Hz), 7.23 (1H, d, J=8.7 Hz), 7.41 (1H, t, J=8.7 Hz), 7.61 (1H, d, J=8.7 Hz)
$^{13}$C NMR (75 MHz, CDCl$_3$) δ 21.2 (t), 27.9 (q), 46.6 (t), 70.0 (t), 82.0 (s), 110.0 (d), 118.5 (s), 121.3 (d), 121.5 (d), 122.4 (s), 127.5 (d), 131.3 (s), 140.8 (s), 167.2 (s), 196.4 (s)
(1-Oxo-3,4-dihydro-1H-2-thia-9-azafluoren-9-yl)acetic acid (Compound 57)
Yield: 66%
IR (KBr) 1720, 1612 cm$^{-1}$
$^1$H NMR (500 MHz, DMSO-d$_6$) δ 3.29 (2H, t, J=6.6 Hz), 3.47 (2H, t, J=6.6 Hz), 5.22 (2H, s), 7.18 (1H, t, J=7.4 Hz), 7.41 (1H, t, J=7.4 Hz), 7.59 (1H, d, J=7.4 Hz), 7.76 (1H, d, J=7.4 Hz)
$^{13}$C NMR (75 MHz, DMSO-d$_6$) δ 21.7 (t), 30.8 (t), 46.3 (t), 110.8 (d), 120.5 (d), 121.2 (d), 124.0 (s), 126.3 (s), 126.9 (s), 127.0 (s), 138.1 (s), 169.9 (s), 183.0 (s)
6-Methyl-4,9-dihydro-3H-pyrano[3,4-b]indole-1-thione
Yield: 99%
IR (KBr) 3349, 1538 cm$^{-1}$
$^1$H NMR (400 MHz, DMSO-d$_6$) δ 2.38 (3H, s), 3.12 (2H, t, J=6.6 Hz), 4.67 (2H, t, J=6.6 Hz), 7.19 (1H, d, J=8.5 Hz), 7.38 (1H, d, J=8.5 Hz), 7.46 (1H, s), 11.53 (1H, br)
$^{13}$C NMR (75 MHz, DMSO-d$_6$) δ 20.5 (t), 21.1 (q), 71.2 (t), 112.6 (d), 115.6 (s), 120.8 (d), 123.9 (s), 129.0 (d), 129.3 (s), 132.2 (s), 138.0 (s), 197.9 (s)
(6-Methyl-1-thioxo-3,4-dihydro-1H-pyrano[3,4-b]indol-9-yl)acetic acid tert-butyl ester
Yield: 99%
IR (KBr) 1745, 1704, 1523 cm$^{-1}$
$^1$H NMR (500 MHz, CDCl$_3$) δ 1.45 (9H, s), 2.45 (3H, s), 3.15 (2H, t, J=6.4 Hz), 4.67 (2H, t, J=6.4 Hz), 5.50 (2H, brs), 7.16 (1H, d, J=8.6 Hz), 7.28 (1H, d, J=8.6 Hz), 7.42 (1H, s)
$^{13}$C NMR (75 MHz, CDCl$_3$) δ 20.8 (q), 20.9 (t), 27.5 (q), 46.3 (t), 69.7 (t), 81.4 (s), 109.4 (d), 117.7 (s), 120.3 (d), 122.1 (s), 129.2 (d), 130.3 (s), 131.0 (s), 139.1 (s), 166.9 (s), 196.0 (s)
(6-Methyl-1-oxo-3,4-dihydro-1H-2-thia-9-azafluoren-9-yl)acetic acid (Compound 58)
Yield: 70%
IR (KBr) 1715, 1625 cm$^{-1}$
$^1$H NMR (500 MHz, DMSO-d$_6$) δ 2.41 (3H, s), 3.27 (2H, t, J=6.8 Hz), 3.47 (2H, t, J=6.8 Hz), 5.18 (2H, s), 7.25 (1H, d, J=8.5 Hz), 7.50 (1H, t, J=8.5 Hz), 7.54 (1H, s)
$^{13}$C NMR (75 MHz, DMSO-d$_6$) δ 21.0 (q), 21.7 (t), 30.8 (t), 46.3 (t), 110.5 (d), 120.2 (d), 124.2 (s), 125.7 (s), 127.1 (s), 128.9 (d), 129.4 (s), 136.7 (s), 169.9 (s), 182.8 (s)
6-tert-Butyl-4,9-dihydro-3H-pyrano[3,4-b]indole-1-thione
Yield: 95%
IR (KBr) 3373, 1541 cm$^{-1}$
$^1$H NMR (500 MHz, CDCl$_3$) δ 1.38 (9H, s), 3.18 (2H, t, J=6.9 Hz), 4.74 (2H, t, J=6.9 Hz), 7.35 (1H, d, J=8.2 Hz), 7.50 (1H, d, J=8.2 Hz), 7.56 (1H, s), 8.80 (1H, br) (6-tert-Butyl-1-thioxo-3,4-dihydro-1H-pyrano[3,4-b]indol-9-yl)acetic acid tert-butyl ester
Yield: 95%
IR (KBr) 1748, 1527 cm$^{-1}$
$^1$H NMR (400 MHz, CDCl$_3$) δ 1.36 (9H, s), 1.45 (9H, s), 3.17 (2H, t, J=6.4 Hz), 4.66 (2H, t, J=6.4 Hz), 5.47 (2H, brs), 7.19 (1H, d, J=8.7 Hz), 7.53 (1H, d, J=8.7 Hz), 7.55 (1H, s)
$^{13}$C NMR (75 MHz, CDCl$_3$) δ 21.3 (t), 27.9 (q), 31.4 (q), 34.5 (s), 46.6 (t), 69.9 (t), 81.8 (s), 109.7 (d), 116.7 (d), 118.6 (s), 122.0 (s), 126.5 (d), 131.4 (s), 139.3 (s), 144.2 (s), 167.3 (s), 196.3 (s)
(6-tert-Butyl-1-oxo-3,4-dihydro-1H-2-thia-9-azafluoren-9-yl)acetic acid (Compound 59)
Yield: 66%
IR (KBr) 1727, 1623 cm$^{-1}$
$^1$H NMR (500 MHz, DMSO-d$_6$) δ 1.35 (9H, s), 3.31 (2H, t, J=6.3 Hz), 3.46 (2H, t, J=6.3 Hz), 5.19 (2H, brs), 7.52 (2H, brs), 7.67 (1H, brs)
$^{13}$C NMR (75 MHz, DMSO-d$_6$) δ 21.7 (t), 31.4 (q), 34.4 (s), 46.3 (t), 110.4 (d), 116.1 (d), 123.7 (s), 125.8 (s), 126.5 (s), 127.1 (s), 136.6 (s), 143.0 (s), 170.0 (s), 182.8 (s)
(6-Benzyl-1-oxo-3,4-dihydro-1H-2-thia-9-azafluoren-9-yl) acetic acid tert-butyl ester
(6-Benzyl-1-oxo-3,4-dihydro-1H-2-thia-9-azafluoren-9-yl)acetic acid (Compound 60)
Yield: 48%
$^1$H NMR (500 MHz, DMSO-d$_6$) δ 3.26 (2H, t, J=6.8 Hz), 3.46 (2H, t, J=6.8 Hz), 4.03 (2H, s), 5.18 (2H, s), 7.14-7.30 (6H, brm), 7.52 (1H, d, J=8.5 Hz), 7.62 (1H, s)
$^{13}$C NMR (75 MHz, DMSO-d$_6$) δ 21.7 (t), 30.8 (t), 41.0 (t), 46.4 (t), 110.9 (d), 120.3 (d), 124.1 (s), 125.7 (s), 126.0 (d), 127.2 (s), 128.2 (d), 128.4 (d), 128.6 (d), 133.6 (s), 141.6 (s), 169.9 (s), 182.9 (s)
(6-Methoxy-1-oxo-3,4-dihydro-1H-2-thia-9-azafluoren-9-yl)acetic acid tert-butyl ester
(6-Methoxy-1-oxo-3,4-dihydro-1H-2-thia-9-azafluoren-9-yl)acetic acid (Compound 61)
$^1$H NMR (300 MHz, DMSO-d$_6$) δ 3.28 (2H, t, J=6.6 Hz), 3.47 (2H, t, J=6.6 Hz), 3.81 (3H, s), 5.18 (2H, s), 7.05 (1H, dd, J=9.1, 2.5 Hz), 7.22 (1H, d, J=2.5 Hz), 7.52 (1H, d, J=9.1 Hz)
$^{13}$C NMR (75 MHz, DMSO-d$_6$) δ 21.8 (t), 30.8 (t), 46.4 (t), 55.4 (q), 101.0 (d), 111.9 (d), 118.6 (d), 124.2 (s), 125.6 (s), 127.3 (s), 133.7 (s), 154.1 (s), 170.0 (s), 182.8 (s)

6-Cyclohexyl-4,9-dihydro-3H-pyrano[3,4-b]indole-1-thione

Yield: 95%
IR (KBr) 3348, 1541 cm$^{-1}$ (6-Cyclohexyl-1-thioxo-3,4-dihydro-1H-pyrano[3,4-b]indol-9-yl)acetic acid tert-butyl ester Yield: 93%
IR (KBr) 1740, 1525 cm$^{-1}$
$^1$H NMR (500 MHz, CDCl$_3$) δ 1.28 (1H, m), 1.38-1.48 (4H, m), 1.46 (9H, s), 1.76 (1H, m), 1.85-1.92 (4H, m), 2.59 (1H, m), 3.17 (2H, t, J=6.4 Hz), 4.67 (2H, t, J=6.4 Hz), 5.49 (2H, brs), 7.19 (1H, d, J=8.8 Hz), 7.33 (1H, d, J=8.8 Hz), 7.44 (1H, s)
$^{13}$C NMR (75 MHz, CDCl$_3$) δ 21.6 (t), 26.2 (t), 27.0 (t), 28.2 (q), 34.9 (t), 44.5 (d), 46.9 (t), 70.2 (t), 82.3 (s), 111.0 (d), 118.5 (s), 118.6 (d), 122.7 (s), 128.2 (d), 131.7 (s), 140.1 (s), 141.6 (s), 167.6 (s), 196.6 (s)

(6-Cyclohexyl-1-oxo-3,4-dihydro-1H-2-thia-9-azafluoren-9-yl)acetic acid (Compound 62)

Yield: 64%
IR (KBr) 1717, 1619 cm$^{-1}$
$^1$H NMR (500 MHz, CDCl$_3$) δ 1.26-1.32 (1H, m), 1.44 (4H, sext-like, J=12.4 Hz), 1.77 (1H, d-like, J=13.2 Hz), 1.89 (4H, q-like, J=12.4 Hz), 2.60 (1H, t-like, J=11.1 Hz), 3.20 (1H, br), 3.32 (2H, t, J=6.5 Hz), 3.43 (2H, t, J=6.5 Hz), 5.26 (2H, s), 7.21 (1H, d, J=8.5 Hz), 7.33 (1H, d, J=8.5 Hz), 7.45 (1H, s)
$^{13}$C NMR (75 MHz, DMSO-d$_6$) δ 21.7 (t), 25.7 (t), 26.5 (t), 30.8 (t), 34.4 (t), 43.8 (d), 46.3 (t), 110.6 (d), 117.8 (d), 124.0 (d), 126.1 (d), 127.0 (s), 127.1 (s), 137.0 (s), 140.1 (s), 170.0 (s), 182.8 (s)

5,7-Dimethyl-4,9-dihydro-3H-pyrano[3,4-b]indole-1-thione

Yield: 85%
IR (KBr) 3324, 3244, 1527 cm$^{-1}$
$^{13}$C NMR (75 MHz, DMSO-d$_6$) δ 19.1 (q), 21.7 (q), 22.5 (t), 70.8 (t), 109.9 (d), 117.0 (s), 121.3 (s), 123.4 (d), 131.6 (s), 133.0 (s), 136.9 (s), 140.3 (s), 197.5 (s)

(5,7-Dimethyl-1-thioxo-3,4-dihydro-1H-pyrano[3,4-b]indol-9-yl)acetic acid tert-butyl ester Yield: 85%
IR (KBr) 1716, 1515 cm$^{-1}$
$^1$H NMR (500 MHz, CDCl$_3$) δ 1.47 (9H, s), 2.42 (3H, s), 2.59 (3H, s), 3.36 (2H, t, J=6.4 Hz), 4.63 (2H, t, J=6.4 Hz), 5.48 (2H, brs), 6.75 (1H, s), 6.85 (1H, s)
$^{13}$C NMR (75 MHz, CDCl$_3$) δ 19.9 (q), 22.3 (q), 23.7 (t), 28.1 (q), 46.9 (t), 69.7 (t), 82.1 (s), 107.5 (d), 119.6 (s), 119.9 (s), 124.8 (d), 131.3 (s), 133.5 (s), 138.5 (s), 142.1 (s), 167.5 (s), 196.1 (s)

(5,7-Dimethyl-1-oxo-3,4-dihydro-1H-2-thia-9-azafluoren-9-yl)acetic acid (Compound 63)

Yield: 86%
IR (KBr) 1732, 1618 cm$^{-1}$
$^1$H NMR (500 MHz, DMSO-d$_6$) δ 2.36 (3H, s), 2.60 (3H, s), 3.44 (2H, t, J=6.1 Hz), 3.47 (2H, t, J=6.1 Hz), 5.14 (2H, s), 6.74 (1H, s), 7.17 (1H, s)
$^{13}$C NMR (75 MHz, DMSO-d$_6$) δ 20.3 (q), 21.7 (q), 23.8 (t), 30.4 (t), 46.3 (t), 107.8 (d), 121.2 (s), 124.1 (s), 126.7 (s), 127.1 (s), 132.6 (s), 136.6 (s), 139.0 (s), 169.9 (s), 182.6 (s)

(5-Chloro-1-oxo-3,4-dihydro-1H-2-thia-9-azafluoren-9-yl)acetic acid tert-butyl ester (5-Chloro-1-oxo-3,4-dihydro-1H-2-thia-9-azafluoren-9-yl)acetic acid (Compound 64)

Yield: 67%
$^1$H NMR (500 MHz, DMSO-d$_6$) δ 3.48 (2H, t, J=6.6 Hz), 3.65 (2H, t, J=6.6 Hz), 5.24 (2H, s), 7.21 (1H, d, J=8.6 Hz), 7.35 (1H, t, J=8.6 Hz), 7.62 (1H, d, J=8.6 Hz)
$^{13}$C NMR (75 MHz, DMSO-d$_6$) δ 23.0 (t), 30.2 (t), 46.7 (t), 110.3 (d), 120.8 (s), 121.5 (d), 125.0 (s), 127.0 (d), 126.9 (s), 127.0 (s), 127.1 (s), 128.1 (s), 139.3 (s), 169.6 (s), 183.3 (s)

4,6,7,8,9,11-Hexahydro-3H-2-oxa-11-aza-benzo[b]fluorene-1-thione $^1$H NMR (500 MHz, DMSO-d$_6$) δ 1.82-1.84 (4H, m), 2.88-2.90 (4H, m), 3.12 (2H, t, J=6.4 Hz), 4.72 (2H, t, J=6.4 Hz), 7.09 (1H, s), 7.31 (1H, s), 8.61 (1H, br)
$^{13}$C NMR (75 MHz, DMSO-d$_6$) δ 20.6 (t), 22.8 (t), 23.0 (t), 29.2 (t), 29.9 (t), 71.1 (t), 111.6 (d), 115.9 (s), 120.5 (d), 122.4 (s), 130.1 (s), 132.0 (s), 137.4 (s), 138.6 (s), 197.6 (s)

(1-Thioxo-3,4,6,7,8,9-hexahydro-1H-2-oxa-11-azabenzo[b]fluoren-1'-yl) acetic acid tert-butyl ester Yield: 88%
$^1$H NMR (500 MHz, CDCl$_3$) δ 1.46 (9H, s), 1.82 (4H, br), 2.88 (2H, br), 2.92 (2H, br), 3.13 (2H, t, J=6.4 Hz), 4.65 (2H, t, J=6.4 Hz), 5.46 (2H, brs), 6.95 (1H, s), 7.33 (1H, s)
$^{13}$C NMR (75 MHz, CDCl$_3$) δ 21.4 (t), 23.1 (t), 23.2 (t), 28.0 (q), 29.5 (t), 30.7 (t), 46.7 (t), 69.9 (t), 81.9 (s), 109.2 (d), 118.4 (s), 120.5 (d), 121.0 (s), 131.3 (s), 131.5 (s), 138.8 (s), 140.2 (s), 167.6 (s), 196.3 (s)

(1-Oxo-3,4,6,7,8,9-hexahydro-1H-2-thia-11-azabenzo[b]fluoren-11-yl)acetic acid (Compound 65)

Yield: 67%
$^1$H NMR (300 MHz, DMSO-d$_6$) δ 1.76 (4H, br), 2.85 (4H, d-like, J=6.1 Hz), 3.22 (2H, t, J=6.6 Hz), 3.43 (2H, t, J=6.6 Hz), 5.13 (2H, s), 7.26 (1H, s), 7.42 (1H, s)
$^{13}$C NMR (75 MHz, DMSO-d$_6$) δ 21.8 (t), 22.8 (t), 23.0 (t), 29.1 (t), 30.1 (t), 46.2 (t), 109.5 (d), 119.9 (d), 122.6 (s), 125.9 (s), 126.8 (s), 130.0 (s), 137.3 (s), 137.4 (s), 170.0 (s), 182.5 (s)

(8-Thioxo-1,3,4,8,10,11-hexahydro-2H-9-oxa-7-azabenzo[c]fluoren-7-yl)acetic acid tert-butyl ester Yield: 88%
$^1$H NMR (500 MHz, CDCl$_3$) δ 1.46 (9H, s), 1.85 (4H, br), 2.80 (2H, t-like, J=6.1 Hz), 3.09 (2H, t-like, J=6.1 Hz), 3.38 (2H, t, J=6.3 Hz), 4.62 (2H, t, J=6.3 Hz), 5.51 (2H, brs), 7.00 (1H, d, J=8.5 Hz), 7.13 (1H, d, J=8.5 Hz)
$^{13}$C NMR (75 MHz, CDCl$_3$) δ 22.5 (t), 22.6 (t), 23.7 (t), 26.8 (t), 27.7 (q), 29.1 (t), 46.4 (t), 69.5 (t), 81.5 (s), 107.3 (d), 118.9 (s), 121.2 (s), 129.3 (d), 129.9 (s), 131.0 (s), 139.7 (s), 167.0 (s), 195.9 (s)

(8-Oxo-1,3,4,8,10,11-hexahydro-2H-9-thia-7-azabenzo[c]fluoren-7-yl)acetic acid (Compound 66)

Yield: 71%
$^1$H NMR (300 MHz, DMSO-d$_6$) δ 1.78 (4H, br), 2.76 (2H, t-like, J=5.5 Hz), 3.13 (2H, t-like, J=5.5 Hz), 3.40 (2H, t, J=6.6 Hz), 3.51 (2H, t, J=6.6 Hz), 5.16 (2H, s), 7.06 (1H, d, J=8.5 Hz), 7.29 (1H, d, J=8.5 Hz)
$^{13}$C NMR (75 MHz, DMSO-d$_6$) δ 22.5 (t), 22.7 (t), 24.3 (t), 27.0 (t), 29.2 (t), 30.4 (t), 46.3 (t), 108.2 (d), 122.9 (s), 126.5 (s), 127.0 (s), 128.5 (s), 129.1 (d), 131.1 (s), 137.0 (s), 169.9 (s), 182.9 (s)

The β-carboline derivative and 1,3,4,9-tetrahydropyrano[3,4-b]indole derivative which are fused tricyclic compounds of the invention exhibit aldose reductase inhibitory activity, while showing low sorbitol dehydrogenase inhibitory activity, demonstrating high enzyme selectivity.

Therefore, the fused tricyclic compound of the invention is useful to treat diseases showing polyol hypermetabolism or overexpression of aldose reductase, for example, as a medicine to cure diabetic complications such as diabetic retinopathy, diabetic nephropathy, and diabetic neuropathy which are considered to be caused by sorbitol accumulation in a polyol pathway, as an agent to treat various cancers such as colon cancer in which the increase in aldose reductase activity is considered to affect cell growth, and a therapeutic agent to treat diseases such as arteriosclerosis, ischemia or reperfusion damage of the heart or brain, systemic inflammatory response syndrome, myocardial disorder or renal failure in a state of sepsis, and the like.

Although only some embodiments of the invention have been described in detail above, those skilled in the art would readily appreciate that many modifications are possible in the embodiments without materially departing from the novel teachings and advantages of the invention. Accordingly, such modifications are intended to be included within the scope of the invention.

What is claimed is:

1. A fused tricyclic compound shown by the following formula:

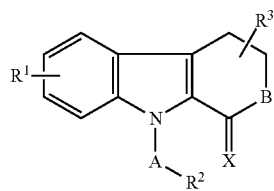

wherein $R^1$ independently represents 1 to 3 atoms or substituents selected from a hydrogen atom, a halogen atom, a substituted or unsubstituted alkyl, cycloalkyl, alkylene, or alkoxy group, and a protected or unprotected hydroxyl or carboxyl group, $R^2$ represents a protected or unprotected carboxyl group, $R^3$ independently represents 1 or 2 atoms or substituents selected from a hydrogen atom, a halogen atom, an oxo group, a substituted or unsubstituted alkyl or alkoxy group, and a protected or unprotected carboxyl group, A represents an alkylene group, B represents an oxygen atom, a sulfur atom, or a group shown by the following formula:

wherein $R^4$ represents an alkyl or aryl group substituted with an aryl, cycloalkyl, or heterocyclic group, and X represents an oxygen atom or a sulfur atom, provided that, when B represents a group shown by the following formula:

wherein $R^4$ represents an alkyl or aryl group substituted with an aryl, cycloalkyl, or heterocyclic group, X represents a sulfur atom.

2. The fused tricyclic compound according to claim 1, wherein B represents an oxygen atom or a sulfur atom.

3. The fused tricyclic compound according to claim 1, wherein B represents a group shown by the following formula:

wherein $R^4$ represents an alkyl or aryl group substituted with an aryl, cycloalkyl, or heterocyclic group, and X represents a sulfur atom.

4. An aldose reductase inhibitor comprising a fused tricyclic compound shown by the following formula:

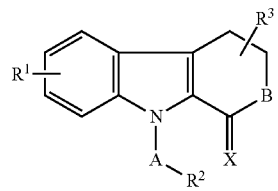

wherein $R^1$ independently represents 1 to 3 atoms or substituents selected from a hydrogen atom, a halogen atom, a substituted or unsubstituted alkyl, cycloalkyl, alkylene, or alkoxy group, and a protected or unprotected hydroxyl or carboxyl group, $R^2$ represents a protected or unprotected carboxyl group, $R^3$ independently represents 1 or 2 atoms or substituents selected from a hydrogen atom, a halogen atom, an oxo group, a substituted or unsubstituted alkyl or alkoxy group, and a protected or unprotected carboxyl group, A represents an alkylene group, B represents an oxygen atom, a sulfur atom, or a group shown by the following formula:

wherein $R^4$ represents an alkyl or aryl group substituted with an aryl, cycloalkyl, or heterocyclic group, and X represents an oxygen atom or a sulfur atom, provided that, when B represents a group shown by the following formula:

wherein $R^4$ represents an alkyl or aryl group substituted with an aryl, cycloalkyl, or heterocyclic group, X represents a sulfur atom.

5. The aldose reductase inhibitor according to claim 4, wherein B represents an oxygen atom or a sulfur atom.

6. The aldose reductase inhibitor according to claim 4, wherein B represents a group shown by the following formula:

wherein $R^4$ represents an alkyl or aryl group substituted with an aryl, cycloalkyl, or heterocyclic group, and X represents a sulfur atom.

7. A therapeutic agent for treating diabetic retinopathy, diabetic nephropathy, diabetic neuropathy, arteriosclerosis, ischemia or reperfusion damage of the heart or brain, systemic inflammatory response syndrome, or renal failure in a state of sepsis, or leukemia comprising a fused tricyclic compound shown by the following formula as a main ingredient:

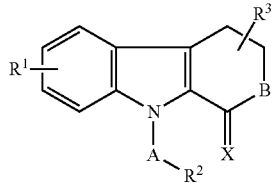

wherein $R^1$ independently represents 1 to 3 atoms or substituents selected from a hydrogen atom, a halogen atom, a substituted or unsubstituted alkyl, cycloalkyl, alkylene, or alkoxy group, and a protected or unprotected hydroxyl or carboxyl group, $R^2$ represents a protected or unprotected carboxyl group, $R^3$ independently represents 1 or 2 atoms or substituents selected from a hydrogen atom, a halogen atom, an oxo group, a substituted or unsubstituted alkyl or alkoxy group, and a protected or unprotected carboxyl group, A represents an alkylene group, B represents an oxygen atom, a sulfur atom, or a group shown by the following formula:

wherein $R^4$ represents an alkyl or aryl group substituted with an aryl, cycloalkyl, or heterocyclic group, and X represents an oxygen atom or a sulfur atom, provided that, when B represents a group shown by the following formula:

wherein $R^4$ represents an alkyl or aryl group substituted with an aryl, cycloalkyl, or heterocyclic group, X represents a sulfur atom.

8. The therapeutic agent according to claim 7, wherein B represents an oxygen atom or a sulfur atom.

9. The therapeutic agent according to claim 7, wherein B represents a group shown by the following formula:

wherein $R^4$ represents an alkyl or aryl group substituted with an aryl, cycloalkyl, or heterocyclic group, and X represents a sulfur atom.

* * * * *